(12) United States Patent
Suzuki

(10) Patent No.: US 8,419,765 B2
(45) Date of Patent: *Apr. 16, 2013

(54) MEDICAL APPARATUS

(75) Inventor: Takayuki Suzuki, Yokohama (JP)

(73) Assignee: Olympus Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/177,778

(22) Filed: Jul. 7, 2011

(65) Prior Publication Data

US 2011/0270272 A1    Nov. 3, 2011

Related U.S. Application Data

(63) Continuation of application No. 10/670,029, filed on Sep. 24, 2003, now Pat. No. 7,985,239, which is a continuation of application No. PCT/JP02/09828, filed on Sep. 25, 2002.

(30) Foreign Application Priority Data

Sep. 25, 2001   (JP) ................................. 2001-292358

(51) Int. Cl.
*A61B 17/28* (2006.01)

(52) U.S. Cl.
USPC .......................................... 606/206; 606/205

(58) Field of Classification Search ................ 606/1, 52, 606/167, 170, 174, 205, 206, 207, 208, 209; 600/567, 564, 562
See application file for complete search history.

(56) References Cited

U.S. PATENT DOCUMENTS

| | | | |
|---|---|---|---|
| 4,715,809 A | 12/1987 | Langhoff et al. | |
| 5,782,834 A | 7/1998 | Lucey et al. | |
| 5,906,630 A | 5/1999 | Anderhub et al. | |
| 6,066,102 A | 5/2000 | Townsend et al. | |
| 6,110,127 A | 8/2000 | Suzuki | |
| 6,689,122 B2 | 2/2004 | Yamamoto | |
| 6,767,349 B2 | 7/2004 | Ouchi | |

(Continued)

FOREIGN PATENT DOCUMENTS

| | | |
|---|---|---|
| JP | 8-509623 | 10/1996 |
| JP | 11-509132 | 8/1999 |

(Continued)

OTHER PUBLICATIONS

International Search Report dated Jan. 14, 2003.

(Continued)

*Primary Examiner* — Tuan V Nguyen
(74) *Attorney, Agent, or Firm* — Scully, Scott, Murphy & Presser, P.C.

(57) ABSTRACT

A medical instrument includes a swingable operating section formed of a pair of forceps which rock around a first rocking axis. A tubular sheath includes a distal end portion situated on a proximal end side of the operating section having a circular-section portion having a circular cross-section perpendicular to a longitudinal central axis and a pair of flat portions formed by cutting the opposite sides of the circular-section portion and in sliding contact with the proximal end portions of the forceps. A manipulator advances and retreats in a longitudinal direction of the sheath, thereby rocking the forceps. A junction connects the manipulator for rocking motion around a second rocking axis with respect to the forceps in the flat portions, and is situated on or near a reference plane passing through the longitudinal central axis of the sheath and extending parallel to the second rocking axis when the operating section is closed.

7 Claims, 18 Drawing Sheets

U.S. PATENT DOCUMENTS

| | | | |
|---|---|---|---|
| 6,964,662 | B2 | 11/2005 | Kidooka |
| 6,969,389 | B2 | 11/2005 | Kidooka |
| 2002/0068946 | A1 | 6/2002 | Kortenbach et al. |
| 2002/0138086 | A1 | 9/2002 | Sizto, Jr. et al. |
| 2002/0198537 | A1 | 12/2002 | Smith et al. |
| 2002/0198538 | A1 | 12/2002 | Kortenbach et al. |
| 2002/0198539 | A1 | 12/2002 | Sixto, Jr. et al. |
| 2002/0198540 | A1 | 12/2002 | Smith et al. |
| 2002/0198541 | A1 | 12/2002 | Smith et al. |
| 2002/0198549 | A1 | 12/2002 | Sizto, Jr. et al. |

FOREIGN PATENT DOCUMENTS

| | | |
|---|---|---|
| JP | 2000-279418 | 10/2000 |
| WO | WO 97/41776 | 11/1997 |
| WO | WO 99/45847 | 9/1999 |

OTHER PUBLICATIONS

European Search Report dated Dec. 30, 2004.

European Seach Report dated Mar. 1, 2006.

U.S. Office Action dated Jul. 5, 2007 of parent case (U.S. Appl. No. 10/670,029).

U.S. Office Action dated Jan. 10, 2008 of parent case (U.S. Appl. No. 10/670,029).

U.S. Office Action dated Sep. 3, 2008 of parent case (U.S. Appl. No. 10/670,029).

U.S. Office Action dated Jun. 10, 2009 of parent case (U.S. Appl. No. 10/670,029).

Notice of Allowance dated Mar. 4, 2011 of parent case (U.S. Appl. No. 10/670,029).

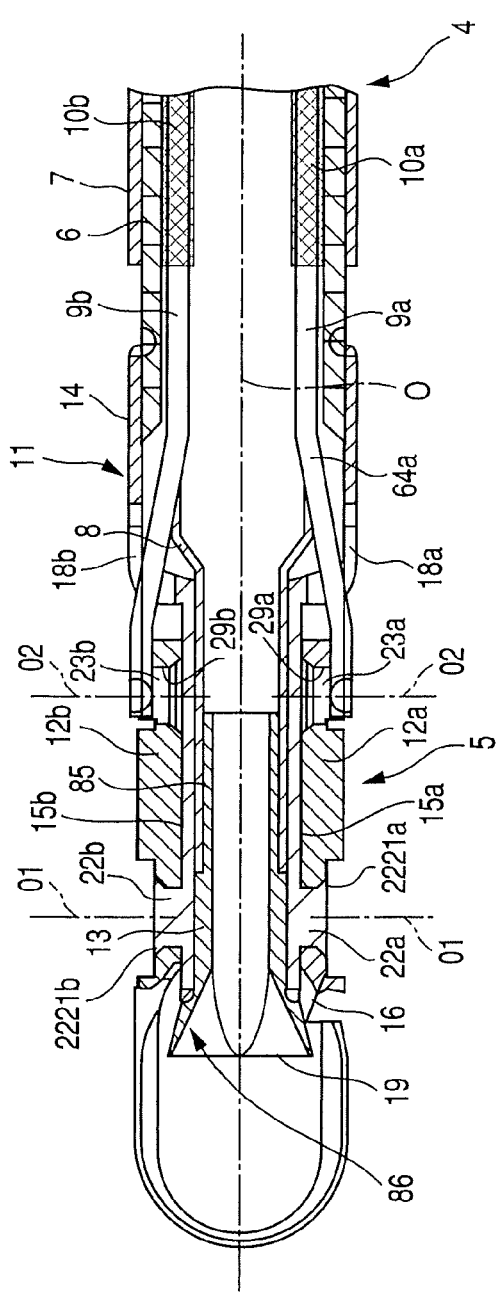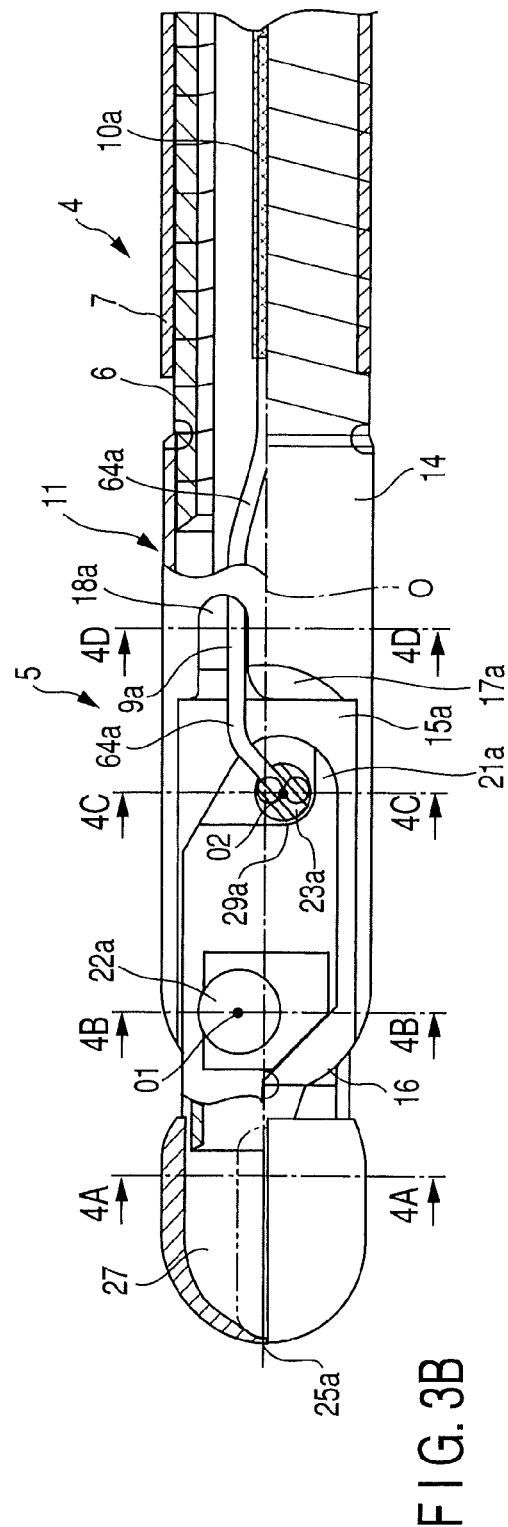

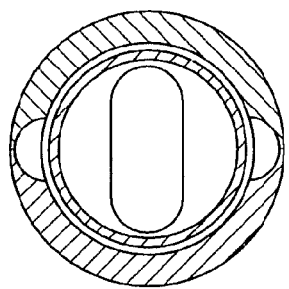
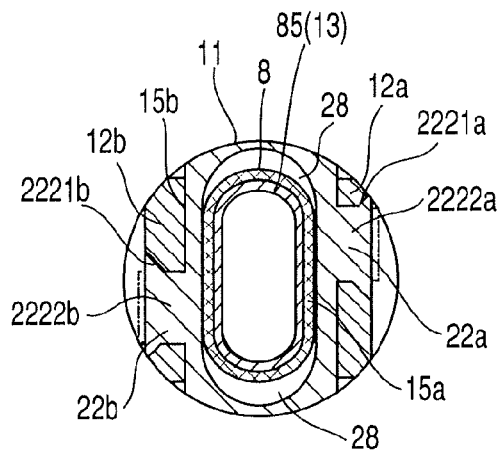
F I G. 4A    F I G. 4B
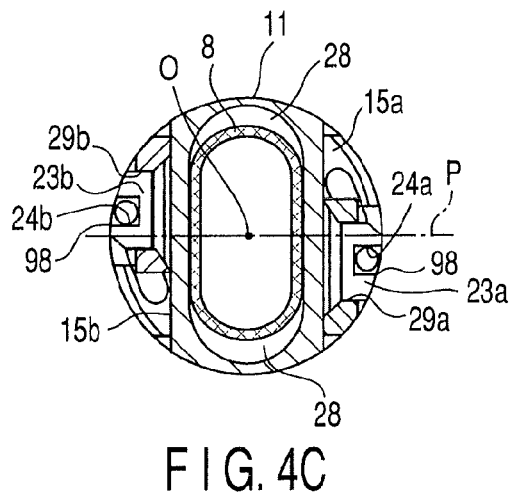
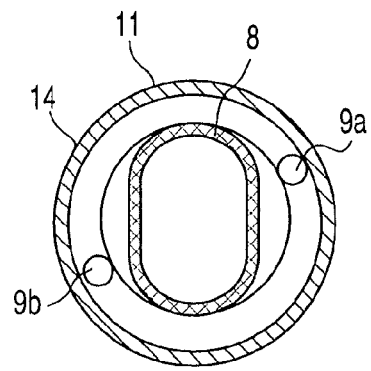
F I G. 4C    F I G. 4D

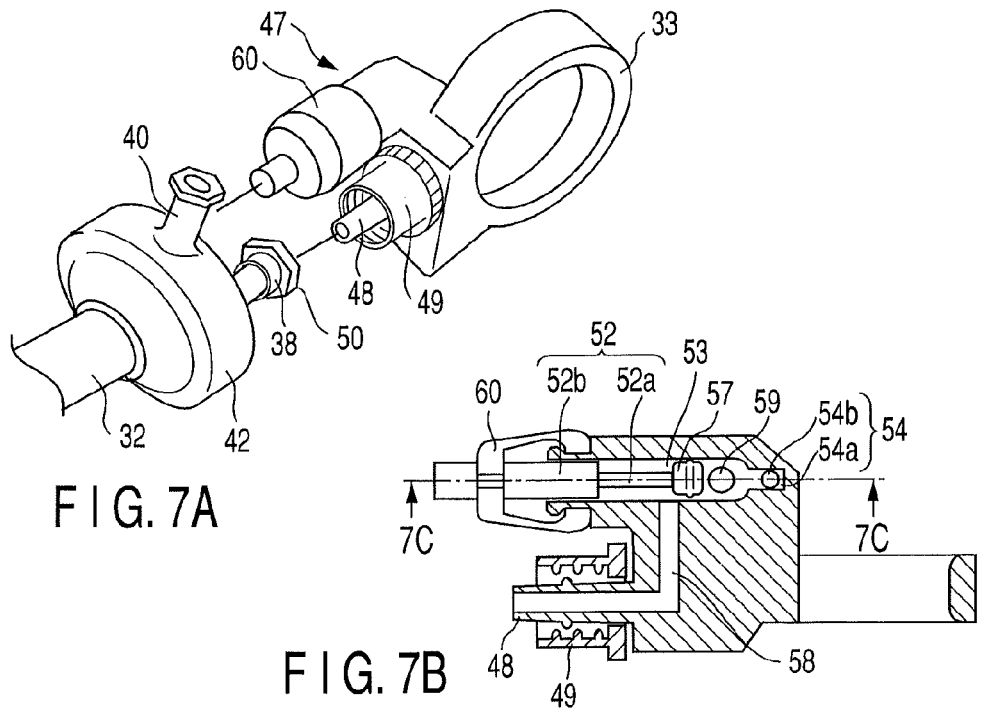
FIG. 7A
FIG. 7B
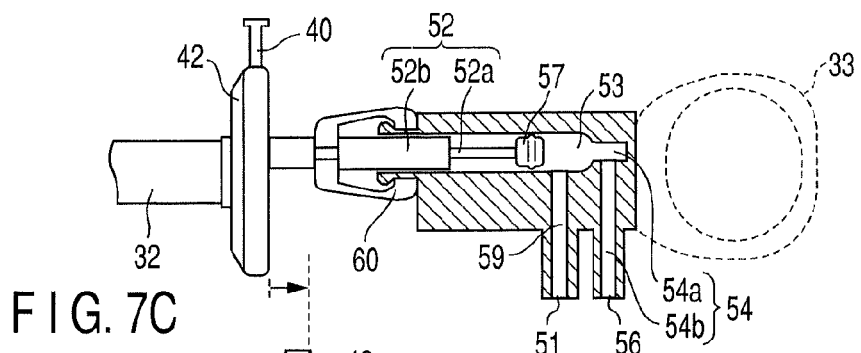
FIG. 7C
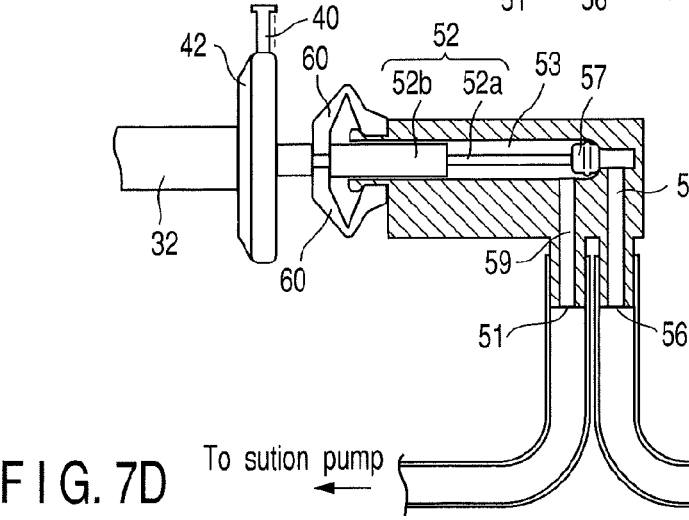
FIG. 7D

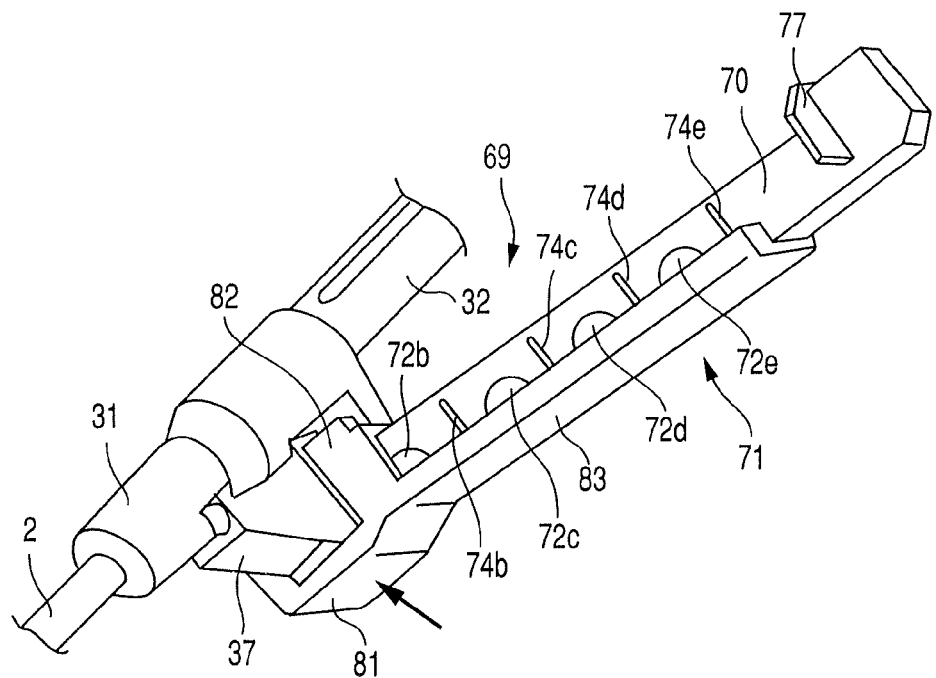
F I G. 8A
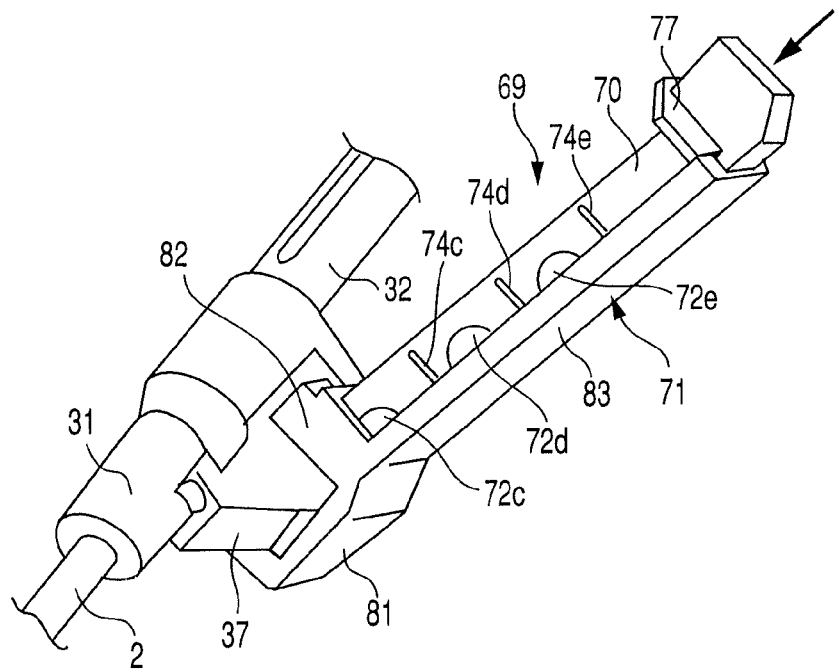
F I G. 8B

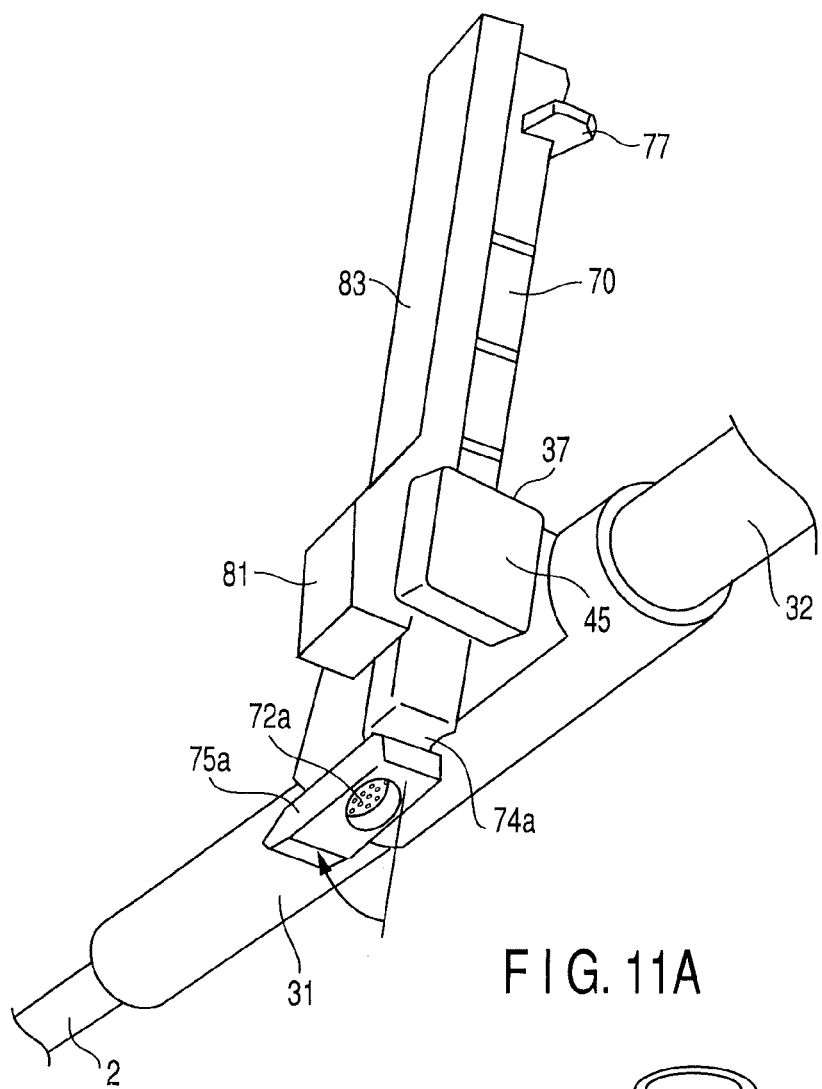
FIG. 11A
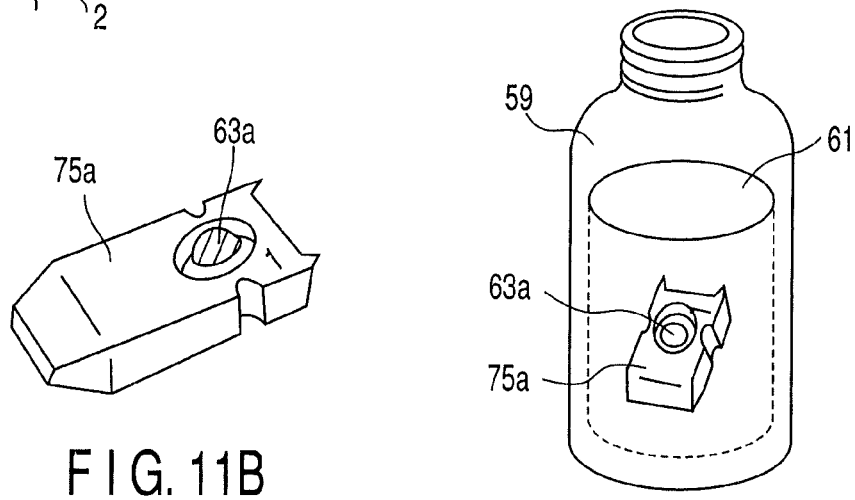
FIG. 11B
FIG. 11C

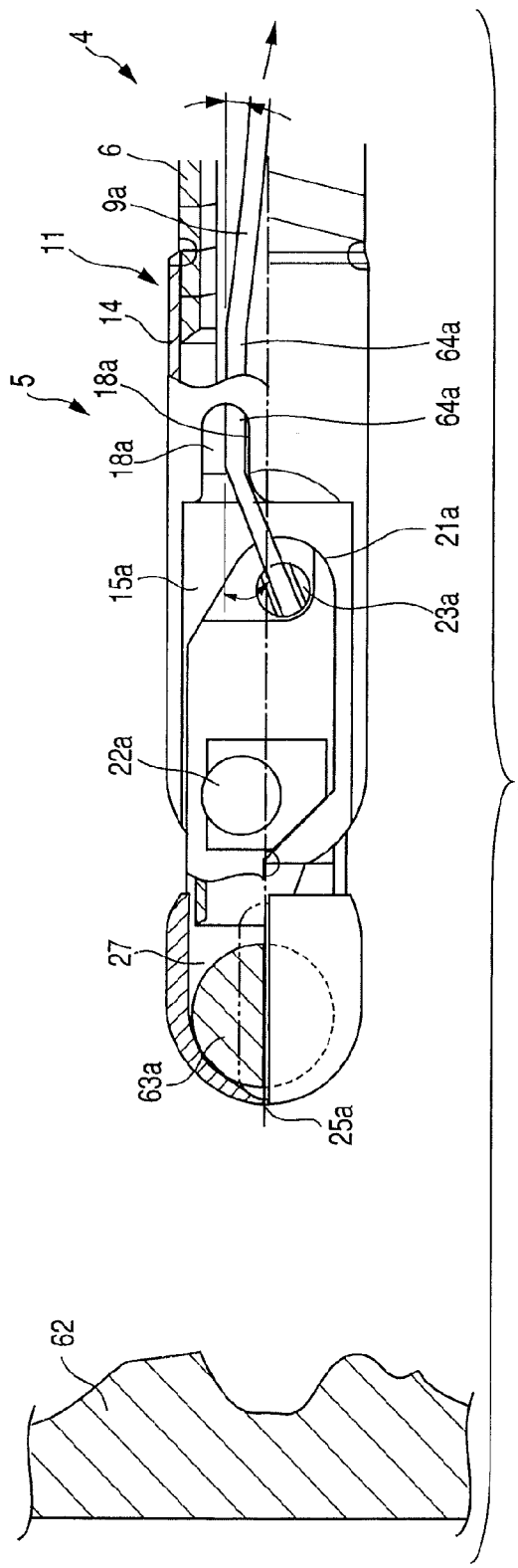
F I G. 13
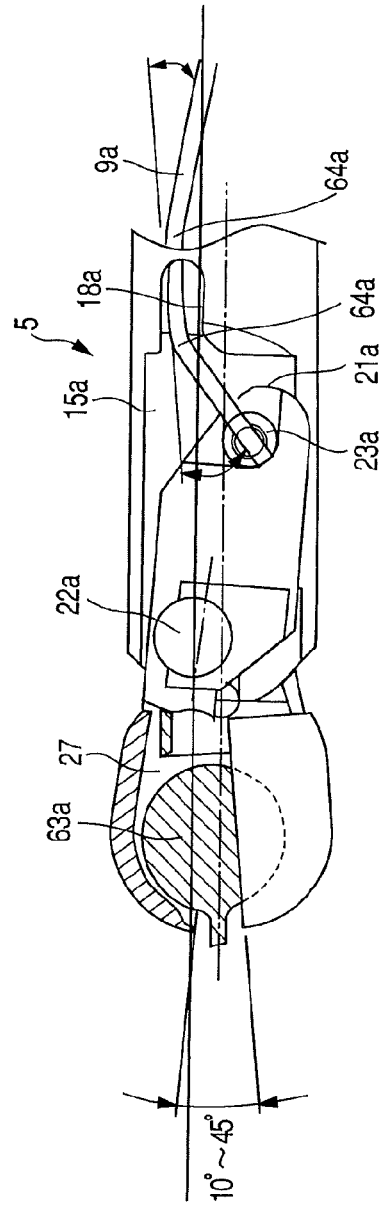
F I G. 14

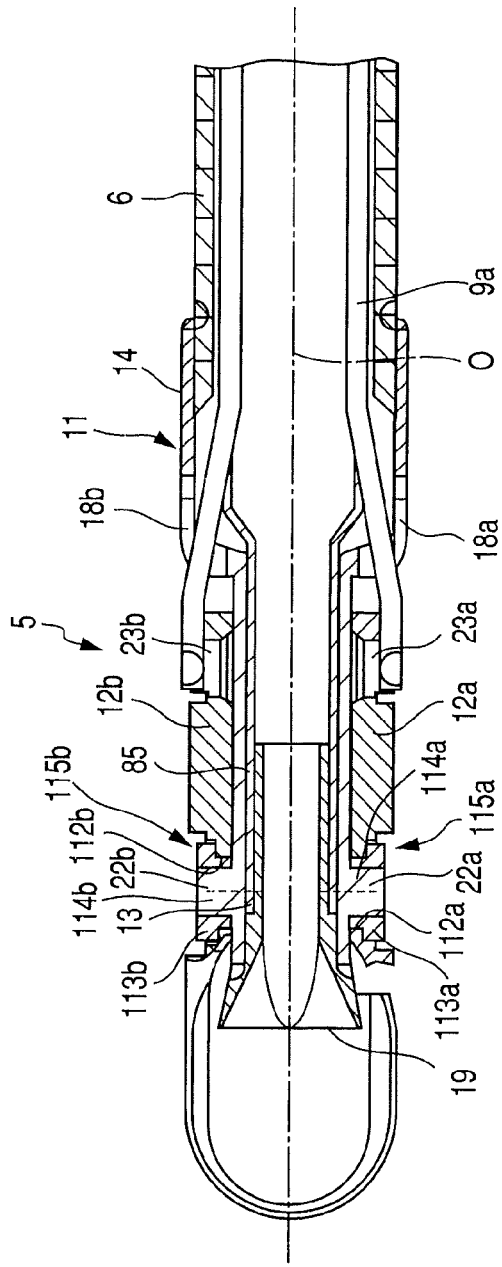
F I G. 15A
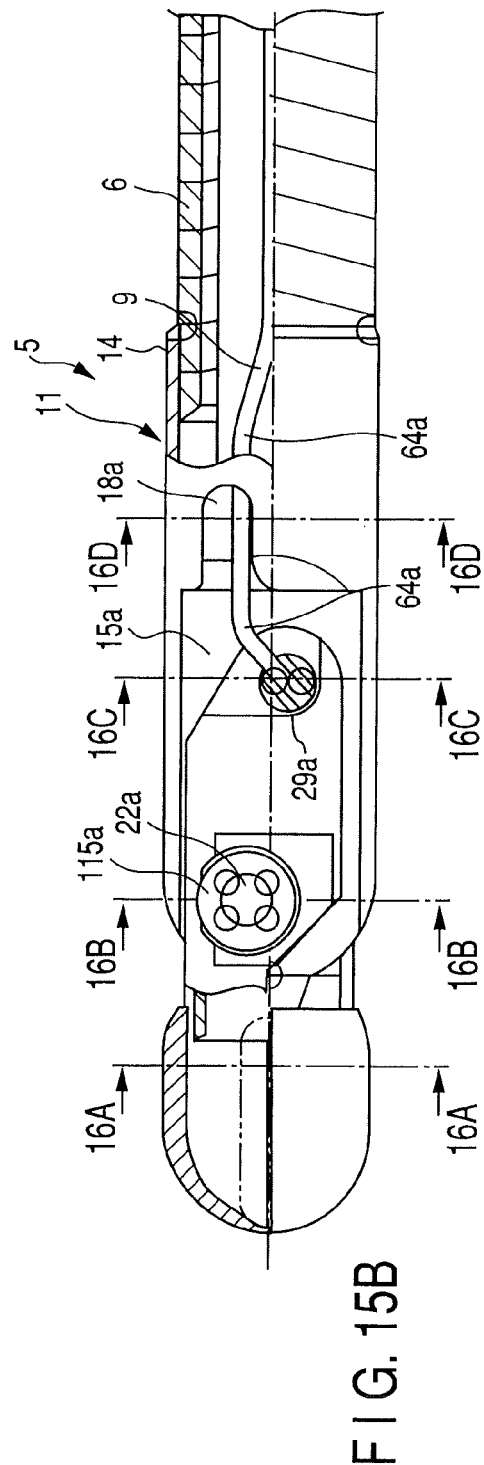
F I G. 15B

MEDICAL APPARATUS

CROSS-REFERENCE TO RELATED APPLICATIONS

This is application is a Continuation Application of U.S. Ser. No. 10/670,029 filed Sep. 24, 2003, now U.S. Pat. No. 7,985,239 issued on Jul. 26, 2011, which is a Continuation Application of PCT Application No. PCT/JP02/09828, filed Sep. 25, 2002, which was not published under PCT Article 21(2) in English.

This application is based upon and claims the benefit of priority from the prior Japanese Patent Application No. 2001-292358, filed Sep. 25, 2001, the entire contents of each of which are incorporated herein by reference.

BACKGROUND OF THE INVENTION

1. Field of the Invention

The present invention relates to a medical instrument.

2. Description of the Related Art

A prior art example of a medical instrument (see Patent Publication No. 2000-279418) for continuously endoscopically picking an organic tissue will now be described with reference to FIGS. 17A to 17D and 18A to 18E.

As shown in FIG. 17A, this conventional medical instrument 201 comprises an insert section 202 that can be inserted into an endoscope and an instrument control section 203 that is fixed to a proximal end portion of the insert section 202. The insert section 202 is composed of a sheath 204 and a tissue picking portion 205 that is fixed to a distal end of the sheath 204.

As shown in FIG. 18A, an inner tube 208 for use as a lumen for excised slice recovery is passed through the bore of the sheath 204. Further, forceps control wires 209a and 209b for operating a pair of forceps 212a and 212b (see FIGS. 17B and 17C), along with the inner tube 208, are passed through the bore of the sheath 204. The respective proximal ends of the control wires 209a and 209b are fixed integrally to a forceps control slider 234 (see FIG. 17A).

As is evident from FIGS. 17B and 17C, the forceps 212a and 212b have movable jaws 220a and 220b on their respective distal end portions. The movable jaws 220a and 220b grasp and excise a part of the organic tissue. Further, the forceps 212a and 212b have rocking arms 221a and 221b for rocking the movable jaws 220a and 220b on their respective proximal end portions. The approximate central portions of the forceps 212a and 212b are mounted on supporting pins 222a and 222b (see FIG. 18B), respectively. The forceps supporting pins 222a and 222b are attached to a tip cover 211, extend through flat portions 215a and 215b, respectively, of the tip cover 211, and can rock independently of each other.

The respective proximal ends of the rocking arms 221a and 221b are rockably fitted with forceps control wire holding pins 223a and 223b for use as rocking pins that hold the forceps control wires 209a and 209b, individually. These forceps control wire holding pins 223a and 223b penetrate through holes 229a and 229b formed in the rocking arms 221a and 221b, respectively.

As is also shown in FIGS. 18A to 18C, a suction nozzle 213 is formed integrally on the distal end of the inner tube 208. The suction nozzle 213 has an oval cross section that is perpendicular to the longitudinal direction of the insert section 202. Further, the distal end portion of the suction nozzle 213 that has a suction port 219 on its distal end projects into a tissue receiving space 227 of the movable jaws 220a and 220b through an opening portion 216 of the tip cover 211.

As shown in FIG. 17A, the instrument control section 203 has a suction port 238 connected to the proximal end of the inner tube 208 and a liquid conveying port 240 connected to the proximal end of a residual space 228. The suction port 238 is to be connected to a negative-pressure generator 235 by means of a tissue recovery container 237 and a suction tube 236. Further, a syringe 239 for use as fluid supply means can be connected to the liquid conveying port 240.

As shown in FIG. 17D, the tissue recovery container 237 is composed of a container housing that has six vials 246a to 246f and six vial inlet holes 249a to 249f provided corresponding to the six vials 246a to 246f, individually. The vials 246a to 246f serve as independent tissue traps that are independent of one another. In this case, the vials 246a to 246f are removably attached to their corresponding vial inlet holes 249a to 249f without failing to maintain airtightness.

The following is a description of treatment for the organic tissue by means of the medical instrument 201 constructed in this manner.

First, the interior of the body cavity is observed through the endoscope as the endoscope and the medical instrument 201 are moved in the body cavity, and the tissue picking portion 205 is guided to a position where it faces a subject tissue of a mucous membrane. Subsequently, the forceps control slider 234 is moved to the distal end side to push out the pair of forceps control wires 209a and 209b to the distal end side. Thereupon, the forceps control wire holding pins 223a and 223b rotate as they move together with the rocking arms 221a and 221b to the distal end side. Accordingly, the forceps 212a and 212b rock around the forceps supporting pins 222a and 222b, respectively, whereupon the movable jaws 220a and 220b swing open around the central axis of the tissue picking portion 205 (see FIGS. 17B and 17C).

When the movable jaws 220a and 220b are open, as shown in FIG. 19, thereafter, edge portions 225a and 225b of the movable jaws 220a and 220b are caused to engage a subject tissue 262. In this state, the forceps control slider 234 is moved to the proximal end side, so that the pair of forceps control wires 209a and 209b are pulled back to the proximal end side. Thereupon, the movable jaws 220a and 220b are closed to excise the subject tissue 262, and a tissue slice 263 is held in the tissue receiving space 227 of the jaws 220a and 220b (see FIG. 20).

When the tissue slice 263 is held and recovered in the tissue receiving space 227 of the jaws 220a and 220b in this manner, the negative-pressure generator 235 is actuated to evacuate air from the inner tube 208 and thus the suction nozzle 213, thereby forming a negative pressure therein. If a fluid is then fed into the residual space 228 in the sheath 204 by means of the syringe 239, the fluid is jetted out into the tissue receiving space 227 of the jaws through the opening portion 216 of the tip cover 211, and runs the tissue slice 263 into the suction nozzle 213. The tissue slice 263 that has been run in the suction nozzle 213, along with the supplied fluid, is sucked into the inner tube 208 under the negative pressure produced by means of the negative-pressure generator 235, and is carried into a suction line 255 of the tissue recovery container 237 through the suction port 238 without jamming. The tissue slice 263 that is carried into the suction line 255 is captured by a mesh filter 252a of the vial 246a. Further, the fluid that is sucked in together with the tissue slice 263a to the suction line 255 passes through the mesh filter 252a and a vial through hole 251a, and is sucked into the negative-pressure generator 235.

In the conventional medical instrument 201 constructed in this manner, the forceps control wires 209a and 209b are fixed by spreading, laser welding, etc. after they are passed through forceps control wire holding grooves 224a and 224b formed in the forceps control wire holding pins 223a and 223b. Since the forceps control wire holding pins 223a and 223b are spaced individually outward from the central axis plane of the forceps (or the plane of contact between the edge portions 225a and 225b of the movable jaws) (that is, the forceps control wire holding pins 223a and 223b are located at a good distance from a plane that passes through the longitudinal central axis of the tissue picking portion 205 (tip cover 211) and extends parallel to the longitudinal central axis of the forceps control wire holding pins 223a and 223b), outward end faces 223f of the forceps control wire holding pins 223a and 223b are obliquely formed to match a circumferential surface C of the forceps (see FIG. 18C). This is done because the outer diameter of the medical instrument must be made smaller than the inner diameter of a forceps channel of the endoscope, since the instrument is inserted in the forceps channel when it is used. In fixing the forceps control wires 209a and 209b to the forceps control wire holding grooves 224a and 224b in the forceps control wire holding pins 223a and 223b by spreading or laser welding, however, a satisfactory connection space (working space) for the forceps control wires 209a and 209b cannot be secured with use of the inclined working plane. Thus, positioning and fixing operations are harder than when a substantially horizontal plane is used. Naturally, in order to give priority to workability, the respective outward end faces 223f of the forceps control wire holding pins 223a and 223b may possibly be formed to be substantially horizontal surfaces in the state of FIG. 18C where the forceps control wire holding pins 223a and 223b are spaced outward from the central axis plane of the forceps. In this case, however, the corner portions of the substantially horizontal surfaces project from the circumferential surface, so that the maximum outer diameter increases. Thus, the resistance of insertion into the endoscope is so high that the operating efficiency lowers.

In the conventional medical instrument 201 constructed in this manner, moreover, the forceps supporting pins 222a and 222b are attached to the tip cover 211 and extend through the flat portions 215a and 215b, respectively, of the tip cover 211. Therefore, head portions 300 of the forceps supporting pins 222a and 222b are bound to project into the bore of the tip cover 211, so that the size of the suction nozzle 213 that is passed through the bore is restricted inevitably.

In the conventional medical instrument 201 constructed in this manner, furthermore, a part 264 of the tissue slice 263, excised and recovered, is inevitably nipped between the edge portions 225a and 225b of the movable jaws 220a and 220b when the subject tissue 262 is grasped and excised by means of the movable jaws 220a and 220b (see FIG. 20). This is because cutting edges on the edge portions 225a and 225b of the movable jaws 220a and 220b cannot completely excise the tissue. More specifically, the tissue picking portion 205 is separated from the subject tissue 262 without releasing the tissue, whereby the tissue is finally torn away. When the part 264 of the tissue slice 263 is thus nipped between the edge portions 225a and 225b of the movable jaws 220a and 220b, it is hard to move the tissue slice 263 into the suction port 219 if a negative pressure is applied to the suction port 219 to reflux the fluid to the suction port 219 through the opening portion 216 of the tip cover 211.

Naturally, in this case, the nipped tissue 264 can be released if the forceps control slider 234 is moved to the distal end side to open the movable jaws 220a and 220b. If the movable jaws 220a and 220b are fully opened, however, the tissue slice 263 inevitably adheres to the movable jaw 220a or 220b and leaves the suction port 219. In consequence, it is hard to suck in and recover the tissue. If the fluid is jetted out through the opening portion 216 of tip cover 211 in this state, the tissue slice 263 may possibly fall off the tissue picking portion 205 under the jet pressure of the fluid.

In order to move the tissue slice 263 successfully to the suction port 219 while releasing the nipped tissue 264, therefore, the movable jaws 220a and 220b should be opened slightly or by half at the most. However, the operator requires skill and subtle manipulation to operate the forceps control slider 234, thereby moderately opening the movable jaws 220a and 220b. Thus, the treatment inevitably takes extra time.

BRIEF SUMMARY OF THE INVENTION

The object of the present invention is to provide a medical instrument that enjoys high operating efficiency and assembling performance.

The above object is achieved by the following medical instrument. The medical instrument comprises: an openable/closable operating section formed of a pair of forceps which rock around a first rocking axis; a tubular sheath having a distal end portion situated on a proximal end side of the operating section, the distal end portion having a circular-section portion having a circular cross section perpendicular to a longitudinal central axis thereof and a pair of flat portions formed by cutting the opposite sides of the circular-section portion and in sliding contact with respective proximal end portions of the forceps; manipulators which advance and retreat in a longitudinal direction of the sheath, thereby rocking the forceps around the first rocking axis; and junctions which connect the manipulators for rocking motion around a second rocking axis with respect to the forceps in the flat portions, the junctions being situated on or near a reference plane passing through the longitudinal central axis of the sheath and extending parallel to the second rocking axis when the operating section is closed.

BRIEF DESCRIPTION OF THE SEVERAL VIEWS OF THE DRAWING

FIG. 3A is a lateral sectional view of the distal end portion of the medical instrument of FIG. 1;

FIG. 3B is a longitudinal sectional view of the distal end portion of the medical instrument of FIG. 1;

FIG. 4A is a sectional view taken along line 4A-4A of FIG. 3B;

FIG. 4B is a sectional view taken along line 4B-4B of FIG. 3B;

FIG. 4C is a sectional view taken along line 4C-4C of FIG. 3B;

FIG. 4D is a sectional view taken along line 4D-4D of FIG. 3B;

FIG. 7A is a perspective view of a ring valve body;

FIG. 7B is a side sectional view of the ring valve body of FIG. 7A;

FIG. 7C is a sectional view taken along line E-E of FIG. 7B;

FIG. 7D is a sectional view corresponding to FIG. 7C, in which a direction of suction is switched;

FIG. 8A is a perspective view of a tissue recovery trap;

FIG. 8B is a perspective view showing the way the tissue recovery trap in the state of FIG. 8A is pushed in;

FIG. 11A is a perspective view showing the way one trap is severed from the trap body;

FIG. 11B is a perspective view of the severed trap;

FIG. 11C is a perspective view showing the severed trap in a sample bottle;

FIG. 13 is a view showing a state in which the forceps in the state of FIG. 12 are closed to recover and hold a tissue slice therein;

FIG. 14 is a view showing a state in which the forceps in the state of FIG. 13 are released from an operating force and opened for a given angle;

FIG. 15A is a lateral sectional view of the distal end portion of a medical instrument according to a second embodiment of the present invention;

FIG. 15B is a longitudinal sectional view of the distal end portion of the medical instrument according to the second embodiment of the present invention;

DETAILED DESCRIPTION OF THE INVENTION

Embodiments of the present invention will now be described with reference to the drawings.

Figure 1:
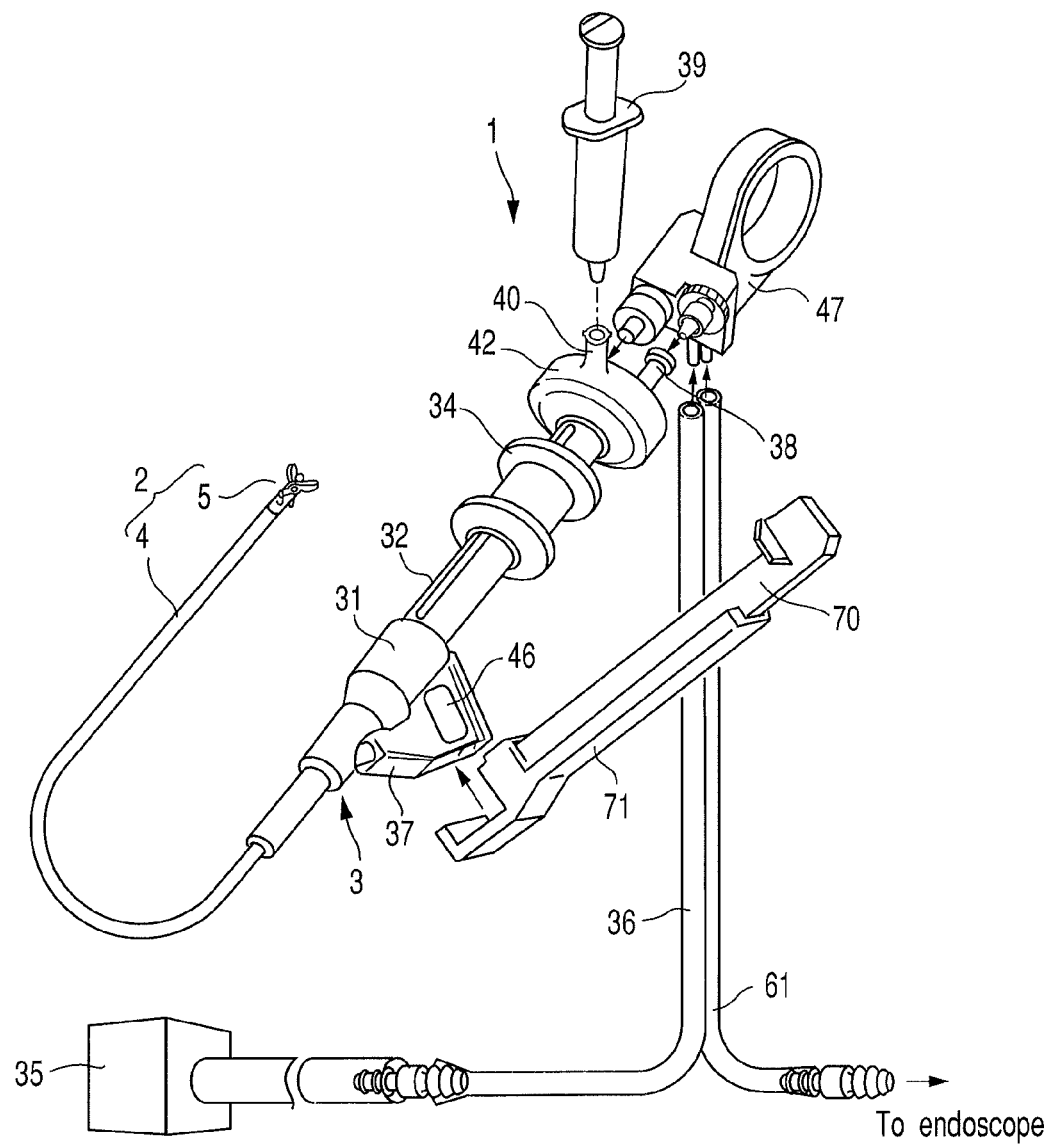
FIG. 1 is a perspective view of a medical instrument according to a first embodiment of the present invention.
Figure 2A:
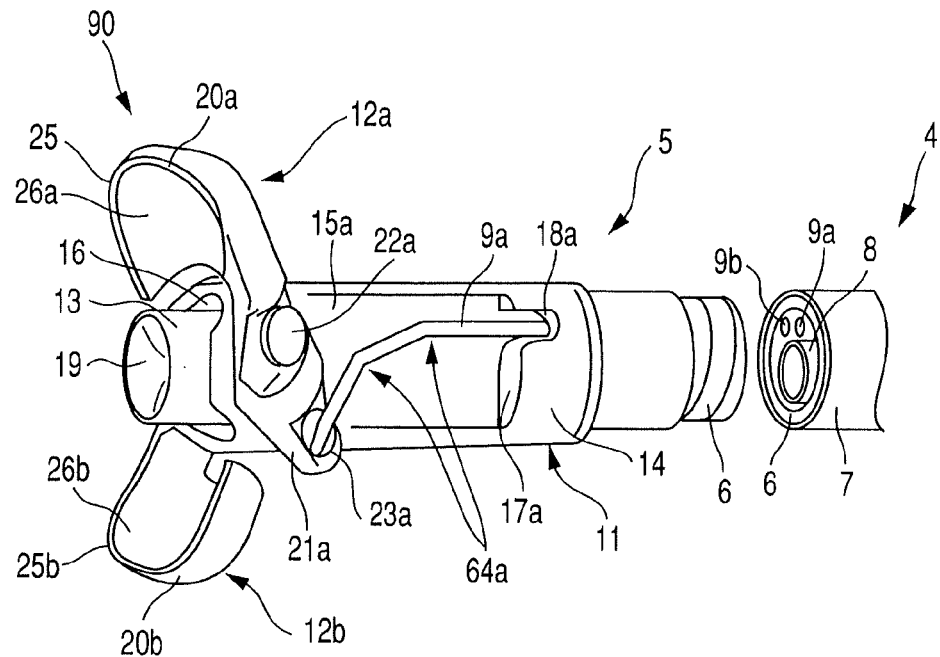
FIG. 2A is an enlarged perspective view of the distal end portion of the medical instrument of FIG. 1.
Figure 2B:
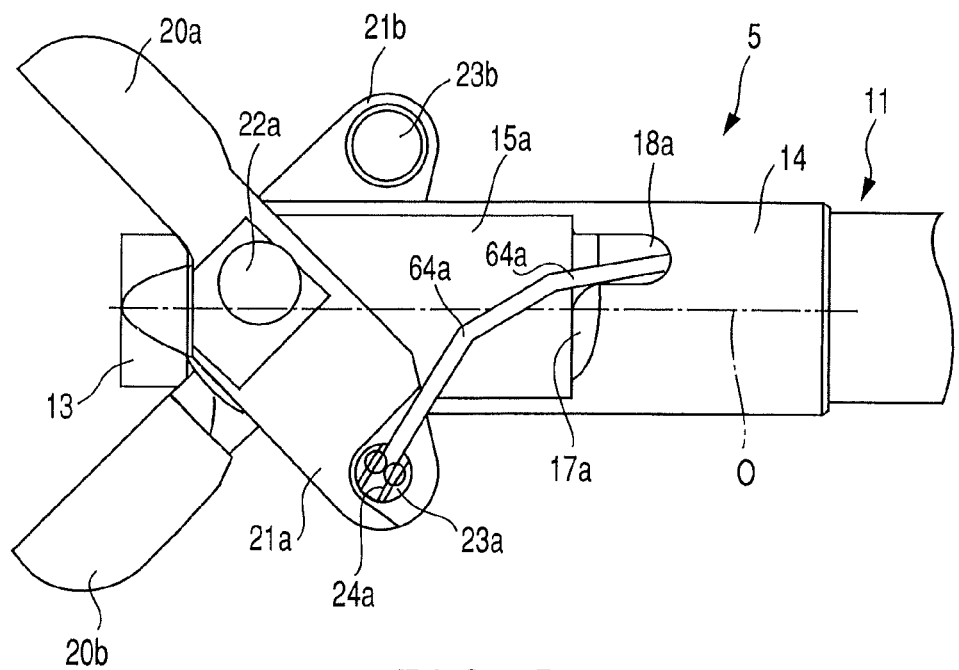
FIG. 2B is an enlarged side view of the distal end portion of the medical instrument of FIG. 1.

FIGS. 1 to 14 show a first embodiment of the present invention. As shown in FIG. 1, a medical instrument 1 of the present embodiment comprises an insert section 2 and an instrument control section 3. The insert section 2 can be inserted into a forceps channel of an endoscope (not shown), and can be inserted together with the endoscope into the body cavity. The instrument control section 3 is fixed integrally to a proximal end of the insert section 2. The insert section 2 is composed of a sheath 4 and a tissue picking portion 5 that is fixed integrally to a distal end of the sheath 4.

As shown in FIG. 3B, the sheath 4 is composed of a sheath inner wall 6 and a sheath skin 7 that protects the outer surface of the sheath inner wall 6. For example, the sheath inner wall 6 used is a closely-wound coil (not shown) formed of a stainless steel wire that is rolled into a rectangular cross section. Thus, the stiffness of the closely-wound coil itself and the sheath 4 can be enhanced, and a wide bore can be secured in the sheath 4.

The sheath skin 7 is formed by coating the outer surface of the sheath inner wall 6 with a chemical substance, such as tetrafluoroethylene, low-density polyethylene, or high-density polyethylene. Since these chemical substances ensure a smooth outer surface after coating, the sheath 4 can be easily inserted into the forceps channel of the endoscope. Since these chemical substances are highly airtight and watertight, moreover, the airtightness and watertightness of the sheath 4 can be maintained.

Thus, the sheath 4 has a dual structure including the sheath inner wall 6 and the sheath skin 7. Accordingly, the sheath 4 can enjoy durability to resist movement that is involved in organic tissue picking operation by means of the medical instrument 1 and the endoscope. Further, the sheath 4 can enjoy flexibility such that it can smoothly bend to match the internal shape of the body cavity. Furthermore, the airtightness and watertightness of the bore of the sheath 4 can be maintained.

As shown in FIG. 3A, an inner tube 8 is passed through the bore of the sheath 4. The inner tube 8 is formed as a lumen for recovery excised slice that transfers an implant (excised slice) 63a (see FIG. 13), which is excised from an organic tissue (internal tissue) 62 (see FIG. 12) mentioned later, from the distal end of the sheath 4 to the proximal end. Further, the inner tube 8 has its distal end airtightly connected to a suction nozzle 13 (mentioned later) of the tissue picking portion 5 and its proximal end airtightly connected to a tissue trap mounting portion 37 (mentioned later) of the instrument control section 3.

In the present embodiment, the cross section of the inner tube 8 in a direction perpendicular to its longitudinal direction is set to 1.0 mm$^2$ or more. If the inner tube 8 is sized in this size, the tissue once sucked in through the suction nozzle 13 can be transported to the instrument control section 3 without clogging the inner tube 8. Further, the inner tube 8 is formed of a flexible material that can maintain the airtightness of the region from the suction nozzle 13 to the tissue trap mounting portion 37. The material may be a chemical substance forming smooth inner and outer surfaces, such as tetrafluoroethylene, low-density polyethylene, or high-density polyethylene, or a superelastic metallic material.

A pair of forceps control wires (manipulators: independent actuator means) 9a and 9b are passed through the bore of the sheath 4, extending throughout its length in the longitudinal direction. These forceps control wires 9a and 9b range with the inner tube 8 as they are passed through the sheath 4. As they are advanced or retreated, a pair of forceps 12a and 12b (mentioned later) can be operated independently. The forceps control wires 9a and 9b have their distal ends connected to the forceps 12a and 12b, respectively, and their proximal ends fixed integrally to a forceps control slider (independent actuator means, mentioned later) 34 (see FIG. 1) of the instrument control section 3. The forceps control wires 9a and 9b are made of a material that cannot easily snap or buckle and is not susceptible to bending, e.g., stainless spring steel wires or monofilament formed of a superelastic wire material.

As shown in FIG. 3A, forceps control wire skins 10a and 10b cover the surfaces of the forceps control wires 9a and 9b, respectively. These forceps control wire skins 10a and 10b are formed of a chemical substance, such as tetrafluoroethylene, low-density polyethylene, or high-density polyethylene, which can form a finished smooth surface. With use of these forceps control wire skins 10a and 10b, the sliding resistance of the forceps control wires 9a and 9b against the inner surface of the sheath inner wall 6 can be lowered.

As shown in FIGS. 2A to 4D, the tissue picking portion 5 is composed of a tip cover 11 for use as a distal end portion, an operating section 90, and the suction nozzle 13 (mentioned later). The tip cover 11 is fixed integrally to the distal end of the sheath 4. The operating section 90 is formed of a pair of forceps 12a and 12b that are rockably supported on the tip cover 11. The suction nozzle 13 is fixed integrally to the distal end of the inner tube 8. The tip cover 11 has a cylinder portion (circular profile portion) 14 on its proximal end side and a pair of flat portions (formed by cutting the opposite sides of the cylinder portion, for example) 15a and 15b on its distal end side. In this case, the flat portions 15a and 15b are arranged symmetrically with respect to a central axis O of the tissue picking portion 5 in a direction perpendicular to the rocking direction of the forceps 12a and 12b. Further, the tip cover 11 is provided with an opening portion 16 at its distal end. The opening portion 16 has an oval cross section that is perpendicular to the central axis O of the tissue picking portion 5 (see FIG. 4C).

Further, the tip cover 11 has forceps control wire outlet portions (abutting portions) 18a and 18b in its transit portions 17a and 17b between the cylinder portion 14 and the flat portions 15a and 15b. The forceps control wires 9a and 9b are led out of the bore of the sheath 4 through the forceps control wire outlet portions 18a and 18b.

The forceps 12a and 12b have a pair of movable jaws 20a and 20b, respectively, on their distal end side. These movable jaws 20a and 20b grasp a part of the organic tissue 62 (see FIG. 12), excise it as a tissue slice 63a (see FIG. 13), and holds the tissue slice 63a. Further, the forceps 12a and 12b have rocking arms 21a and 21b for rocking the movable jaws 20a and 20b around a first rocking axis O1, respectively, on their proximal end side. The rocking arms 21a and 21b are in sliding contact with the flat portions 15a and 15b, respectively.

Forceps supporting pins 22a and 22b having the first rocking axis O1 are formed integrally on the flat portions 15a and 15b, respectively, of the tip cover 11. The respective approximate central portions of the forceps 12a and 12b are mounted on the supporting pins 22a and 22b, respectively. The respective distal ends of the forceps supporting pins 22a and 22b are mechanically spread to form pin flat portions 2221a and 2221b. Thus, the forceps 12a and 12b are rockably supported on the flat portions 15a and 15b, respectively, of the tip cover 11. More specifically, the forceps supporting pins 22a and 22b that define the first rocking axis O1 are composed of shank portions 2222a and 2222b and spread portions 2221a and 2221b (see FIG. 4B). The shank portions 2222a and 2222b protrude radially outward from the flat portions 15a and 15b, respectively. The spread portions 2221a and 2221b are formed on the respective distal ends of their corresponding shank portions 2222a and 2222b, and are larger in outer diameter larger than the shank portions 2222a and 2222b.

Forceps control wire holding pins (junctions) 23a and 23b, which serve as rocking pins for individually holding the forceps control wires 9a and 9b, are mounted on the respective proximal ends of their corresponding rocking arms 21a and 21b. The pins 23a and 23b are rockable around a second rocking axis O2. In this case, the forceps control wire holding pins 23a and 23b penetrate through holes 29a and 29b formed in the rocking arms 21a and 21b, respectively.

One end sides of the forceps control wire holding pins 23a and 23b that face the flat portions 15a and 15b, respectively, of the tip cover 11 have diameter larger than that of the other end sides. Formed on the other end sides of the forceps control wire holding pins 23a and 23b are forceps control wire holding grooves 24a and 24b, which engage and hold the forceps control wires 9a, respectively. After the respective distal end portions of the forceps control wires 9a and 9b are passed through the forceps control wire holding grooves 24a and 24b, respectively, the forceps control wires 9a and 9b and the forceps control wire holding grooves 24a and 24b are subjected to spreading, laser welding, etc. By doing this, the forceps control wires 9a and 9b and the forceps control wire holding pins 23a and 23b are fixed integrally to one another.

When the forceps 12a and 12b are closed, in the present embodiment, moreover, the forceps control wire holding pins 23a and 23b are situated overlapping the central axis O (that is, the forceps control wire holding pins 23a and 23b are situated on or near a reference plane P that passes through the longitudinal central axis O of the sheath 4 and extends parallel to the second rocking axis O2) (see FIGS. 3B and 4C). Therefore, one end face (outward end face) 98 of each of forceps control wire holding pins 23a and 23b that face (or are opposed to) the flat portions 15a and 15b of the tip cover 11 are substantially in the form of a flat surface (see FIG. 4C). As the forceps control wire holding pins 23a and 23b are situated overlapping the central axis O of the tissue picking portion 5, moreover, the forceps supporting pins 22a and 22b and the forceps control wire outlet portions 18a and 18b are situated in positions eccentric to the central axis O of the tissue picking portion 5 (that is, a plane that passes through the first rocking axis O1 and extends parallel to the reference plane P is not coincident with a plane that passes through the second rocking axis O2 and extends parallel to the reference plane P, and the first rocking axis O1 is not on the reference plane P).

A plurality of bent portions 64a and 64b are formed on the respective distal end portions of the forceps control wires 9a and 9b so as to extend along the forceps control wire holding pins 23a and 23b from the forceps control wire outlet portions 18a and 18b. These bent portions 64a and 64b are formed in a manner such that they never touch or interfere with the forceps control wire outlet portions 18a and 18b when the respective distal ends of the movable jaws 20a and 20b are open at an angle wider than about 10° and narrower than 45° (see FIG. 14). When the movable jaws 20a and 20b are fully closed, moreover, the bent portions 64a and 64b touch and interfere with the forceps control wire outlet portions 18a and 18b, whereby they are elastically deformed (see FIG. 13).

At least one of the respective edge portions 25a and 25b of the movable jaws 20a and 20b is formed sharp-edged by cutting or polishing. Further, recesses 26a and 26b are formed inside the movable jaws 20a and 20b, respectively. These paired recesses 26a and 26b cooperate to define a tissue receiving space 27 that holds the tissue slice 63a and prevents it from slipping out. Thus, the respective edge portions 25a and 25b of the movable jaws 20a and 20b are designed to engage each other without a gap.

Preferably, the forceps 12a and 12b are formed of stainless steel material, or a rigid resin, such as ABS resin, or polycarbonate, which has high strength and ensures satisfactory sharpness for an edge tool. Further, the tip cover 11 and the forceps 12a and 12b, which have complicated shapes and require high precision, should be formed by injection-molding a resin or metal or by forging. Thus, mass production can be achieved at low cost.

As mentioned before, the suction nozzle 13 is integrally fixed to the distal end of the inner tube 8. As is evident from FIGS. 2 and 3, the distal end portion of the suction nozzle 13 that has a perfectly circular suction port 19 at its distal end projects into the tissue receiving space 27 of the movable jaws 20a and 20b through the opening portion 16 of the tip cover 11. Further, the tissue receiving space 27 has a circular cross section that is perpendicular to the longitudinal direction of the insert section 2. The outer diameter of the suction port 19 is set so that it can be covered by the circular cross section. A proximal end side portion 85 of the suction nozzle 13 that is situated in the bore of the tip cover 11 has an oval cross section that is perpendicular to the longitudinal direction of the insert section 2. Although it is situated in the bore of the tip cover 11, the proximal end side portion 85 securely enjoys a cross section wide enough to allow the passage of the tissue slice 63a. Further, a taper portion 86 is formed on a transit portion of the suction nozzle 13 that connects the suction port 19 and the proximal end side portion 85. The taper portion 86 smoothly joints the suction port 19, which has the circular cross section, and the inner surface of the proximal end side portion 85.

A residual space 28 for use as a liquid conveying lumen is defined between the tip cover 11 and the suction nozzle 13. The distal end of the residual space 28 communicates with the tissue receiving space 27 of the movable jaws 20a and 20b, while its proximal end is connected to a reflux port 40 (mentioned later) of the instrument control section 3 through the bore of the sheath 4. In the present embodiment, the cross section of the residual space 28 that is perpendicular to its longitudinal direction is adjusted to 0.5 mm$^2$ or more.

Figure 5:
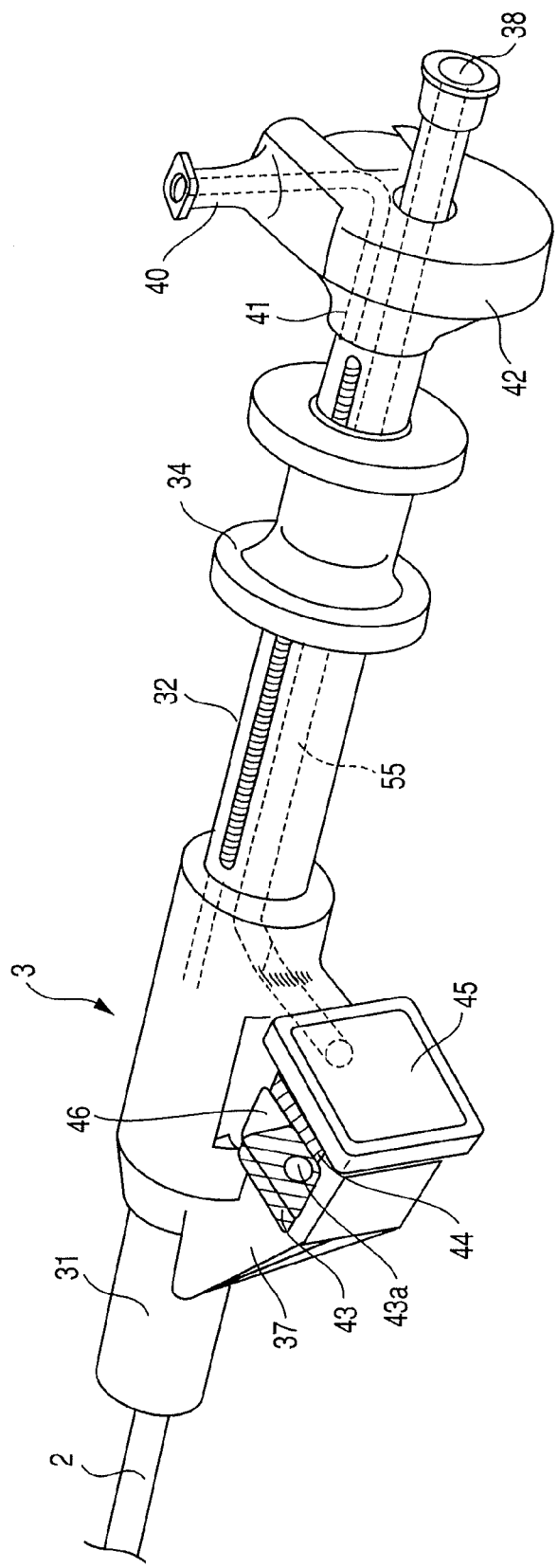
FIG. 5 is a perspective view of an instrument control section of the medical instrument of FIG. 1.
Figure 6:
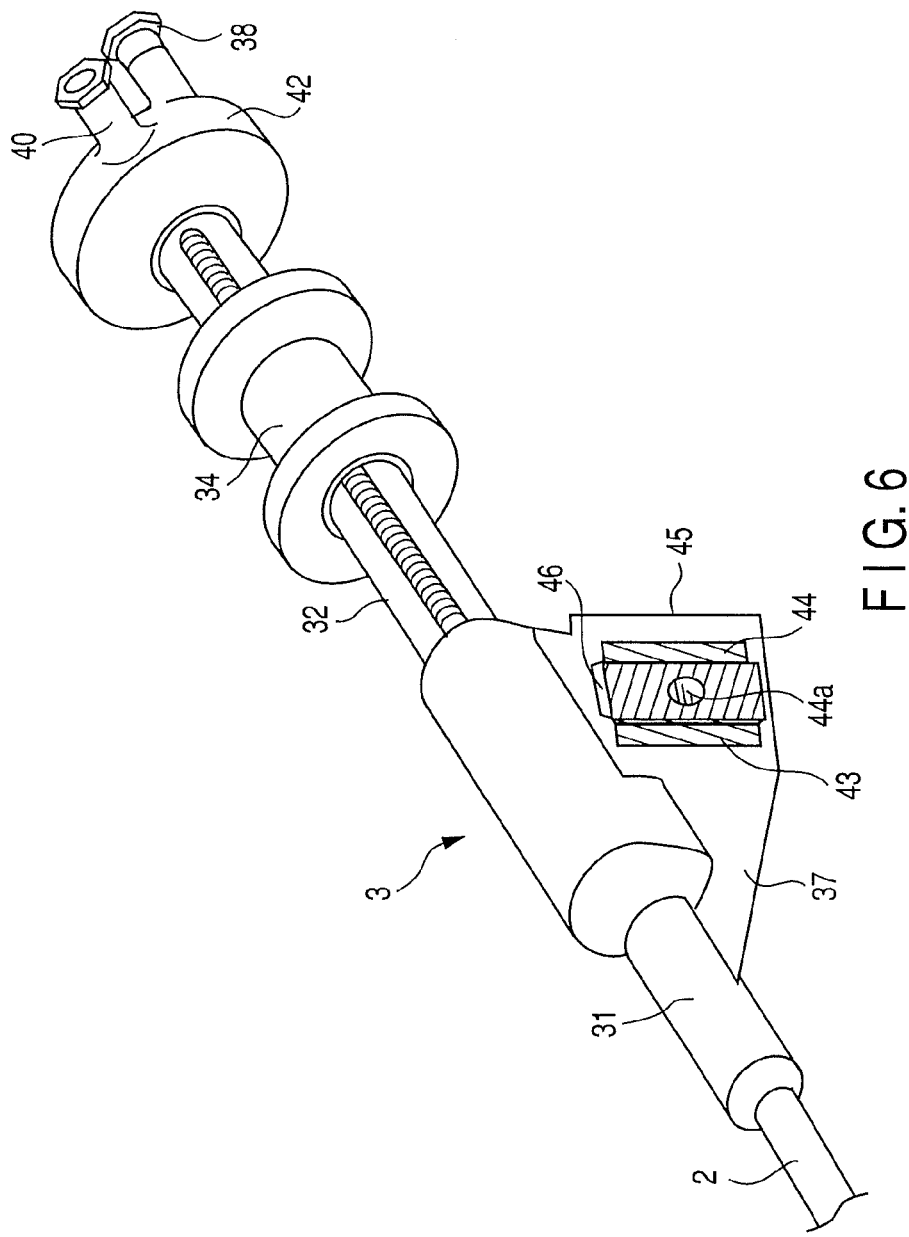
FIG. 6 is a perspective view of the instrument control section of the medical instrument of FIG. 1.

As shown in FIGS. 1, 5 and 6, the instrument control section 3 has a control section body 31, a supporting rod 32, and a ring-shaped forceps control slider (actuator means) 34. The control section body 31 is airtightly connected to the proximal end of the insert section 2. The supporting rod 32 is integrally fixed to the proximal end of the control section body 31 in its longitudinal direction. The forceps control slider 34 is fitted on the supporting rod 32 and is slidable in the longitudinal direction of the supporting rod 32. In this case, the supporting rod 32 penetrates a center hole of the forceps control slider 34 in its axial direction, and a suction control slider 42 is slidably mounted on its proximal end. Accordingly, the forceps control slider 34 can slide in the longitudinal direction of the supporting rod 32 between the control section body 31 and the suction control slider 42. The suction control slider 42 can also slide in the longitudinal direction of the supporting rod 32 on the proximal end side of the forceps control slider 34. The suction control slider 42 is provided with a liquid conveying port 40 that can directly connect a syringe 39 (see FIG. 1) and the like, which will be mentioned later. Further, the inside of the liquid conveying port 40 is lure-tapered to have a smooth surface that facilitates insertion of fluid supply means such as the syringe 39. Besides the syringe 39, a motor-driven liquid conveying pump (not shown) or the like can be used as a fluid source that is connected to the liquid conveying port 40.

The forceps control slider 34 is connected with the respective proximal end portions of the paired forceps control wires 9a and 9b that extend through the interior of the supporting rod 32. If the forceps control slider 34 is moved along the supporting rod 32 toward the distal end (or toward the control section body 31), therefore, the forceps 12a and 12b open in the manner mentioned later. If the forceps control slider 34 is moved along the supporting rod 32 toward the proximal end (or toward the suction control slider 42), on the other hand, the forceps 12a and 12b close in the manner mentioned later.

Further, a suction line 55 is provided in the supporting rod 32 so as to extend covering its overall length. The distal end of the suction line 55 opens in the tissue trap mounting portion 37 (mentioned later). The proximal end of the suction line 55 is connected to a suction port 38 that is set on the proximal end of the supporting rod 32. Furthermore, a liquid conveying line 41 is passed through the interior of the supporting rod 32. The distal end side of the liquid conveying line 41 passes through the interior of the control section body 31 and is airtightly connected to the proximal end of the sheath 4. More specifically, the distal end portion of the liquid conveying line 41 is airtightly connected to the residual space 28 in the sheath 4 in the control section body 31. The proximal end side of the liquid conveying line 41 is airtightly connected to the liquid conveying port 40.

The instrument control section 3 has a tissue trap mounting portion 37 in which the proximal end of the inner tube 8 opens. In the control section body 31, the inner tube 8 is airtightly connected to a front-side opening seal 43 of the tissue trap mounting portion 37, and communicates with an opening 43a of the front-side opening seal 43. The proximal end side of the front-side opening seal 43 is provided with a rear-side opening seal 44 that faces the front-side opening seal 43 at a given distance therefrom. The front-side opening seal 43 and the rear-side opening seal 44 define between them a through hole 46 for trap insertion in which a trap body 70 of a tissue recovery trap 69 (mentioned later) can be inserted.

Further, the proximal end side of the rear-side opening seal 44 is provided with a tissue recognition window 45 that is formed of a transparent material. With use of this tissue recognition window 45, an operator can visually recognize the state of the trap body 70 of the tissue recovery trap 69 to be inserted into the through hole 46 for trap insertion through the rear-side opening seal 44. The distal end of the suction line 55 opens on the lateral side of the internal space of the tissue recognition window 45 in an airtight state, and communicates with an opening 44a of the rear-side opening seal 44.

As shown in FIG. 7A, a ring valve body 47 is removably fixed to the suction port 38 provided on the proximal end of the supporting rod 32. The distal end of the ring valve body 47 is provided with a lure male 48 that is fitted in the suction port 38 and a rock ring 49 that is rockable coaxially with the lure male 48. An internal thread is formed on the inner surface of the rock ring 49. The internal thread is screwed with a projection 50 on the outer surface of the suction port 38. Further, the inner surface of the suction port 38 is formed with a slow lure-tape. The lure male 48 is inserted into the suction port 38 so that the outer surface of the lure male 48 is fitted on the lure-tapered surface of the inner surface of the suction port 38. If the internal thread on the inner surface of the rock ring 49 is caused to engage the projection 50 on the outer surface of the suction port 38 in this state, therefore, the ring valve body 47 can be firmly coupled to the supporting rod 32. A grip ring 33 is provided integrally on the proximal end of the ring valve body 47.

A sliding tubular line 53 is provided in the ring valve body 47. The sliding tubular line 53 forms a sliding path for a valve seat 57 that controls communication between various passages in the ring valve body 47. As a push rod 52 that is coupled to it advances or retreats, the valve seat 57 moves airtightly in contact with the inner surface of the sliding tubular line 53 (or moves in the direction of insertion of the lure male 48 into the suction port 38), and airtightly separates spaces in front and at the back of the sliding tubular line 53.

Further, a release tubular line 54 that communicates with the sliding tubular line 53 at its proximal end is provided in the ring valve body 47. The release tubular line 54 has its inner diameter smaller than that of the sliding tubular line 53 (and therefore, smaller than the outer diameter of the valve seat 57), and is composed of a first pipe portion 54a and a second pipe portion 54b. The first pipe portion 54a extends in the axial direction of the sliding tubular line 53 from the proximal end of the sliding tubular line 53. The second pipe portion 54b extends at right angles to the first pipe portion 54a. The second pipe portion 54b communicates with the outside by means of a return port 56.

An internal communication passage 58 that communicates with the sliding tubular line 53 is provided in the ring valve body 47, and situated on the distal end side more than the release tubular line 54. One end of the internal communication passage 58 opens in a sidewall region of the sliding tubular line 53 at a given distance from the release tubular line 54. The other end of the internal communication passage 58 communicates with the lure male 48 and opens to the outside.

Inside the ring valve body 47, moreover, an external communication passage 59 is located between the release tubular line 54 and the internal communication passage 58. The external communication passage 59 extends parallel to the second pipe portion of the release tubular line 54 and communicates with the outside by means of an external port 51.

The push rod 52 that slides the valve seat 57 in the sliding tubular line 53 is composed of a small-diameter portion 52a on the proximal end side coupled to the valve seat 57 and a large-diameter portion 52b on the distal end side. The large-diameter portion 52b projects from the sliding tubular line 53 without failing to keep the sliding tubular line 53 airtight inside. The large-diameter portion 52b is coupled to the distal end portion of the ring valve body 47 by means of an elastic valve spring 60. More specifically, the distal end portion of the valve spring 60 is fixed to the large-diameter portion 52b of the push rod 52, while the proximal end portion of the valve spring 60 is fixed to the distal end portion of the ring valve body 47. Further, the valve spring 60 always urges the push rod 52 to project from the sliding tubular line 53. The valve spring 60 is formed of a chemical substance, such as silicone rubber, various elastomers, etc. It is contracted by elastic deformation when pushed in and is restored to its original shape when released from the push force.

According to the present embodiment, moreover, the respective lengths of the push rod 52 and the valve spring 60 are set so that the valve seat 57 is situated between the internal communication passage 58 and the external communication passage 59 when the valve spring 60 has its natural length (or is in a fully stretched state) so that the valve seat 57 closes the release tubular line 54 when the valve spring 60 is contracted. Thus, the valve spring 60 has its natural length longer than the distance between the release tubular line 54 and the external communication passage 59.

The external port 51 is connected to a negative-pressure generator 35 (see FIG. 1) by means of a suction tube 36. Further, the return port 56 is connected to a suction input connector (not shown) of the endoscope by means of a return tube 61. A motor-driven vacuum pump, manual vacuum pump, rubber ball, or large-sized syringe may be used for the negative-pressure generator 35 as suction means that is connected to the external port 51.

FIGS. 8A to 11C show details of the tissue recovery trap 69 that is attached to the tissue trap mounting portion 37. As shown in FIG. 8A, the tissue recovery trap 69 is composed of the elongate trap body 70 and a support 71. The trap body 70 can be airtightly inserted into the through hole 46 for trap insertion that is formed in the tissue trap mounting portion 37. The support 71 engages the tissue trap mounting portion 37 and the trap body 70.

Figure 9:
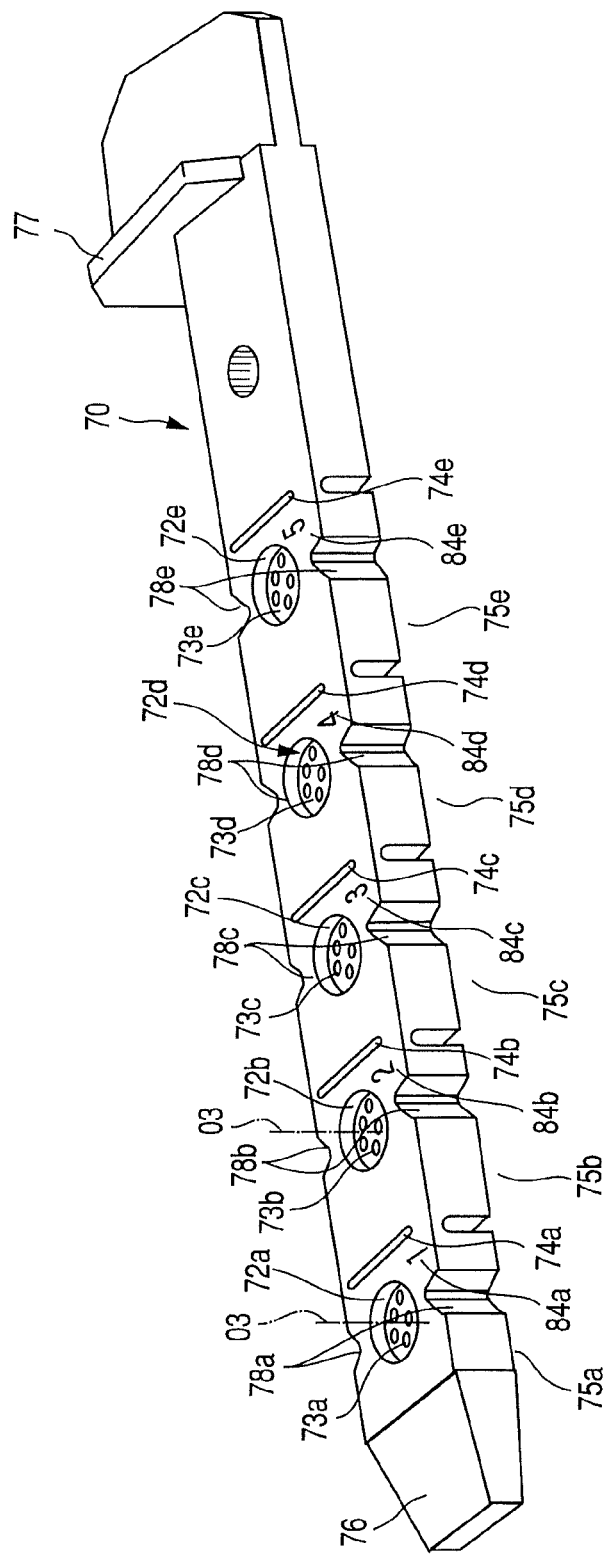
FIG. 9 is a perspective view of a trap body.

As shown in FIG. 9, the trap body 70 is provided with a plurality of depressions 72a to 72e that are arranged in its longitudinal direction. The depressions 72a to 72e are arranged at given spaces in a line in the longitudinal direction of the trap body 70, and their base portions are partially penetrated to the opposite side. Further, the base portions of the depressions 72a to 72e are provided with mesh filters 73a to 73e, respectively, which have a large number of fine orifices.

The depressions 72a to 72e have enough size and depth enough to receive and hold the tissue slices 63a that are excised by means of the forceps 12a and 12b. Preferably, the depressions 72a to 72e have, a diameter of 4 to 10 mm and a depth (depth to the base portions) of about 2 to 5 mm, for example.

Through slits 74a to 74e are formed in the centers between each of depressions 72a to 72e. These through slits 74a to 74e divide the trap body 70 into a plurality of traps 75a to 75e that have the depressions 72a to 72e, respectively.

A taper portion 76 is formed on the distal end of the trap body 70 so as to extend in the longitudinal direction of the trap body 70. A finger knob 77 is formed on the proximal end of the trap body 70. Corresponding to the traps 75a to 75e, respectively, recesses 78a to 78e are formed in side faces (or at least one side face) of the trap body 70 perpendicular to its upper surface in which the depressions 72a to 72e are formed. In the present embodiment, the recesses 78a to 78e are formed in both side faces of the trap body 70, paired corresponding to each of the traps 75a to 75e. Each pair of recesses 78a, 78a (or 78b, 78b; . . . ; 78e, 78e) corresponding to each of the traps 75a to 75e are arranged symmetrically with respect to a central axis O3 of each of the depressions 72a to 72e and extend along the central axis O3 of the depressions 72a to 72e. A plane that passes through each pair of recesses 78a, 78a (or 78b, 78b; . . . ; 78e, 78e) corresponding to each of the traps 75a to 75e passes substantially through the central axis O3 of each corresponding depression 72a (or 72b, 72c, 72d or 72e) and extends substantially at right angles to the longitudinal direction of the trap body 70.

Corresponding to the respective positions of the traps 75a to 75e, markings 84a to 84e are printed in Arabic FIGS. 1 to 5 on the upper surface of the trap body 70. In the present embodiment, the Arabic FIGS. 1 to 5 are emphasized by coating with a paint that inflicts no bodily injury on persons in medical facilities.

Figure 10A:
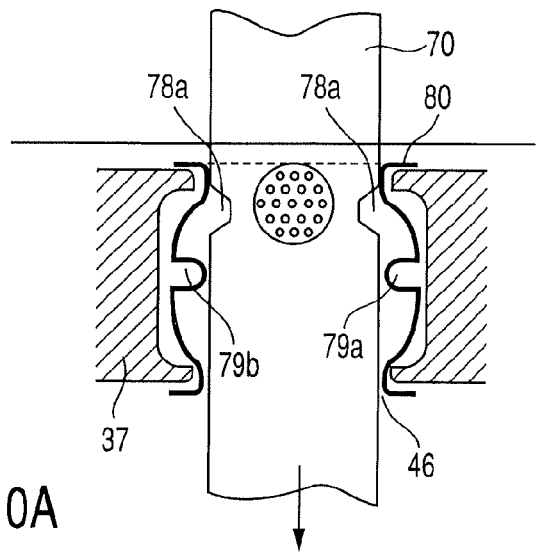
FIG. 10A is a sectional view showing the trap body in engagement with a tissue trap mounting portion.
Figure 10B:
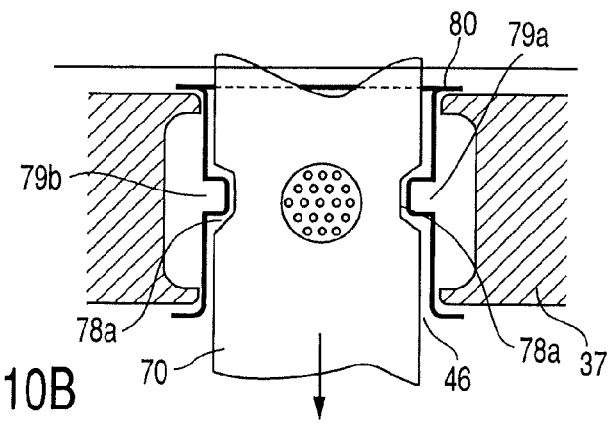
FIG. 10B is a sectional view showing the trap body not in engagement with a tissue trap mounting portion.

The through hole 46 for trap insertion of the tissue trap mounting portion 37 that is fitted with the tissue recovery trap 69 is designed so that the space between the front-side opening seal 43 and the rear-side opening seal 44 that constitute the through hole, is a little shorter than the width of the side faces of the trap body 70 (surfaces in which the recesses 78a to 78e are formed). As shown in FIG. 10A, moreover, the through hole 46 for trap insertion is formed having retractable protrusions 79a and 79b individually on a pair of opposite surfaces that are perpendicular to the front-side opening seal 43 and the rear-side opening seal 44. These protrusions 79a and 79b are formed as a part of a plate spring 80 that is molded by bending a stainless steel sheet, for example. Further, the protrusions 79a and 79b are formed on a plane that connects the inner tube 8 and the suction line 55. They have a size such that they can engage the recesses 78a to 78e in the trap body 70 when they are projecting.

The support 71 is composed of an arm portion 81, an outer fitting portion 82, and a shoulder portion 83 having a U-shaped (groove-shaped) cross section. The arm portion 81 can engage the trap mounting portion 37. The trap body 70 can be inserted into the outer fitting portion 82 in its longitudinal direction. The shoulder 83 extends from the outer fitting portion 82 in the direction opposite to the extending direction of the arm portion 81 has a U-shaped cross section (groove shape), and guides and supports the trap body 70. The shoulder 83 has a groove width substantially equal to the width of the side faces of the trap body 70 in which the recesses 78a to 78e are formed (or the thickness of the trap body 70) and a length substantially equal to the longitudinal dimension of the trap body 70.

The following is a description of the operation of the medical instrument 1 constructed in this manner.

First, the ring valve body 47 is connected to the supporting rod 32 of the instrument control section 3 before treatment. This is achieved by only inserting the lure male 48 into the suction port 38 so that the outer surface of the lure male 48 mates with a lure-tapered surface of the inner surface of the suction port 38 and causing the internal thread on the inner surface of the rock ring 49 to screw-engage the projection 50 on the outer surface of the suction port 38.

Subsequently, the external port 51 is connected to the negative-pressure generator 35 (see FIG. 1) by means of the suction tube 36, and the return port 56 is connected to the suction input connector (not shown) of the endoscope by means of the return tube 61. When the suction control slider 42 is not pulled to the proximal end at this time, the valve spring 60 urges the push rod 52 to project from the sliding tubular line 53. Therefore, the valve seat 57 is situated between the internal communication passage 58 and the external communication passage 59. A negative pressure generated by the negative-pressure generator 35 acts on the endoscope through the external communication passage 59, sliding tubular line 53, release tubular line 54, return port 56, and return tube 61. In this state, therefore, sucking operation can be normally carried out by means of the endoscope.

Before starting treatment, moreover, the trap body 70 and the support 71 are combined so that the arm portion 81 of the support 71 is hooked over and fitted on the trap mounting portion 37, as shown in FIG. 8A. As shown in FIG. 8B, thereafter, the trap body 70 is pushed in the longitudinal direction (direction of the arrow in the drawing). Since the taper portion 76 is formed on the distal end of the trap body 70, the trap body 70 is then smoothly inserted into the through hole 46 for trap insertion that is formed between the front-side opening seal 43 and the rear-side opening seal 44. In this process of insertion, moreover, the protrusions 79a and 79b of the through hole 46 for trap insertion abut individually against the side faces of the trap body 70. If the trap body 70 in this state is further pushed in, the plate spring 80 is deformed so that the protrusions 79a and 79b sink and the trap body 70 is inserted deeper (see FIG. 10A). When the recesses 78a on the extreme distal end side of the trap body 70 reach the respective positions of the protrusions 79a and 79b, the protrusions 79a and 79b are projected to engage the recesses 78a by means of the repulsive force of the plate spring 80 (see FIG. 10B). When the protrusions 79a and 79b are in engagement with the recesses 78a, moreover, the respective centers of the depression 72a and the mesh filter 73a are aligned with the respective centers of the proximal end opening of the inner tube 8, opening 43a of the front-side opening seal 43, opening 44a of the rear-side opening seal 44, and distal end opening of the suction line 55, based on the aforesaid positional relation between the depression 72a and the recesses 78a. Further, the space between the front-side opening seal 43 and the rear-side opening seal 44 is a little shorter than the thickness of the trap body 70 (width of the side faces). When the trap body 70 is inserted so that the protrusions 79a and 79b are in engagement with the recesses 78a, therefore, the inner tube 8, front-side opening seal 43, rear-side opening seal 44, and suction line 55 are connected airtightly, so that an external inflow of air is cut off.

Treatment is started when these preparations are completed. In this treatment, the interior of the body cavity is observed through the endoscope as the endoscope and the medical instrument 1 are moved in the body cavity, and the tissue picking portion 5 is guided to a position where it faces the subject tissue 62 (see FIGS. 12 and 13) of a mucous membrane. Subsequently, the forceps control slider 34 is moved to the distal end side to push out the pair of forceps control wires 9a and 9b to the distal end side. Thereupon, the distal end side of the forceps control wires 9a and 9b is pushed out to the outside of the distal end of the insert section 2 through the forceps control wire outlet portions 18a and 18b. Accordingly, the forceps control wire holding pins 23a and 23b that are fixed integrally to the forceps control wires 9a and 9b rock as the rocking arms 21a and 21b that support them are pushed out toward the distal end side of the insert section 2. Since the forceps control wires 9a and 9b are provided with the bent portions 64a and 64b in this case, the movable jaws 20a and 20b of the forceps 12a and 12b rock independently around the forceps supporting pins 22a and 22b. Thus, the forceps 12a and 12b open on either side of the central axis of the tissue picking portion 5.

Figure 12:
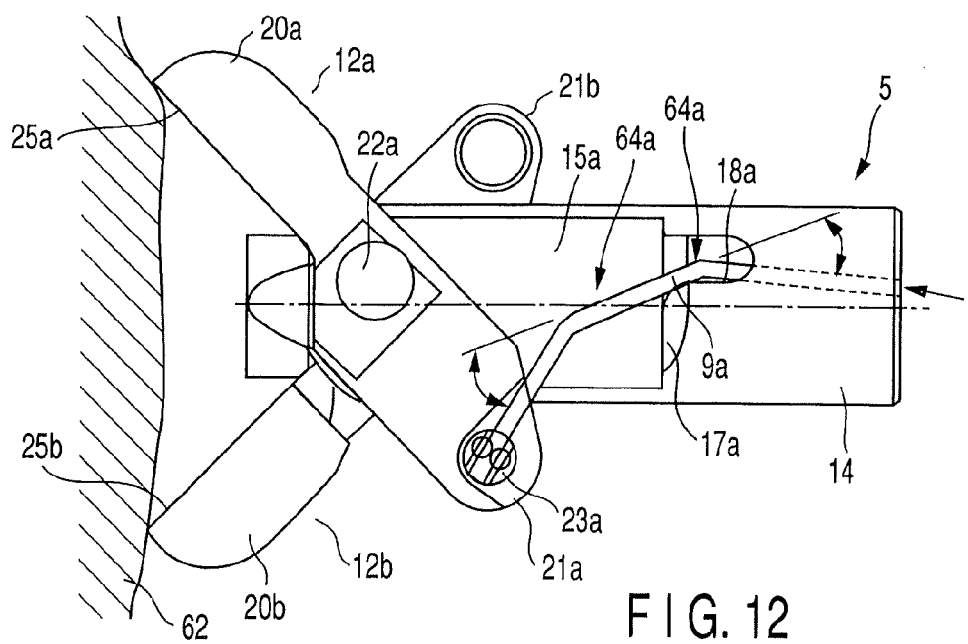
FIG. 12 is a view showing the medical instrument of FIG. 1 having its forceps open and held against a tissue.
Figure 16A:
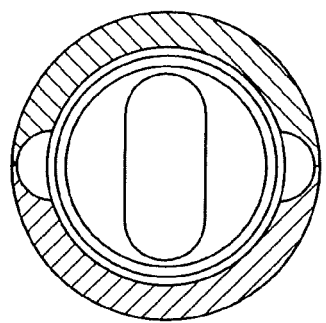
FIG. 16A is a sectional view taken along line 16A-16A of FIG. 15B.
Figure 16B:
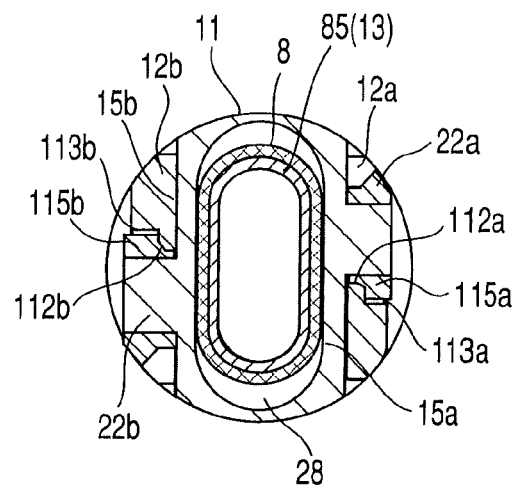
FIG. 16B is a sectional view taken along line 16B-16B of FIG. 15B.
Figure 16C:
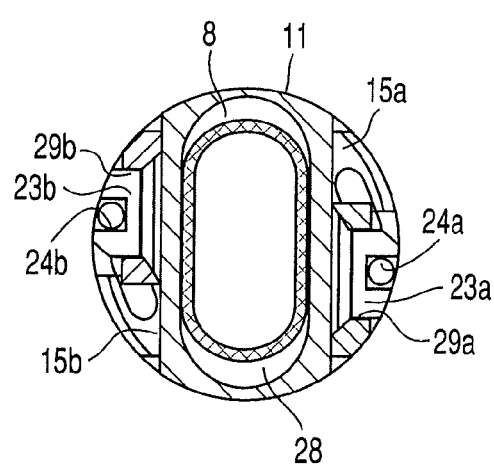
FIG. 16C is a sectional view taken along line 16C-16C of FIG. 15B.
Figure 16D:
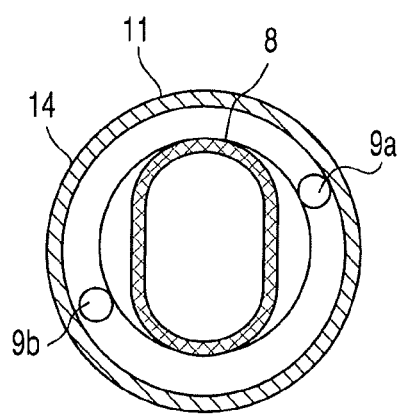
FIG. 16D is a sectional view taken along line 16D-16D of FIG. 15B.
Figure 17B:
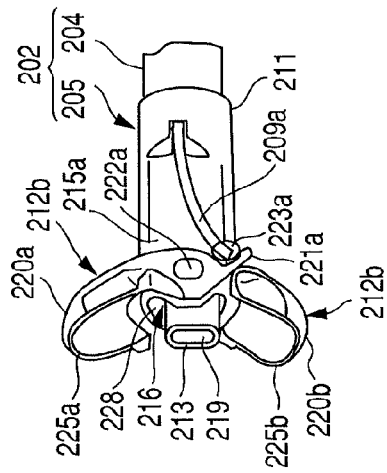
FIG. 17B is a perspective view of the distal end portion of the medical instrument of FIG. 17A.
Figure 17C:
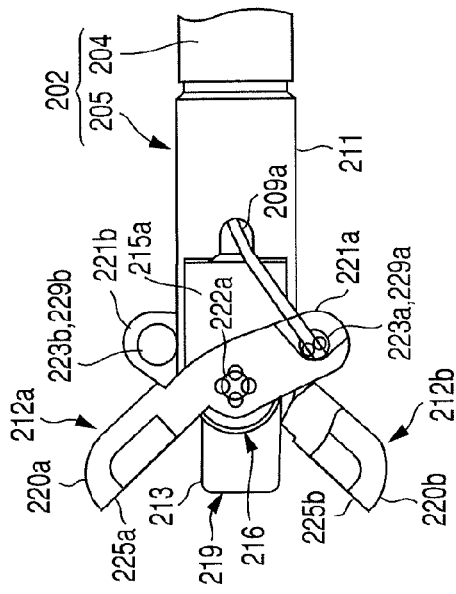
FIG. 17C is a side view of the distal end portion of the medical instrument of FIG. 17A.
Figure 17A:
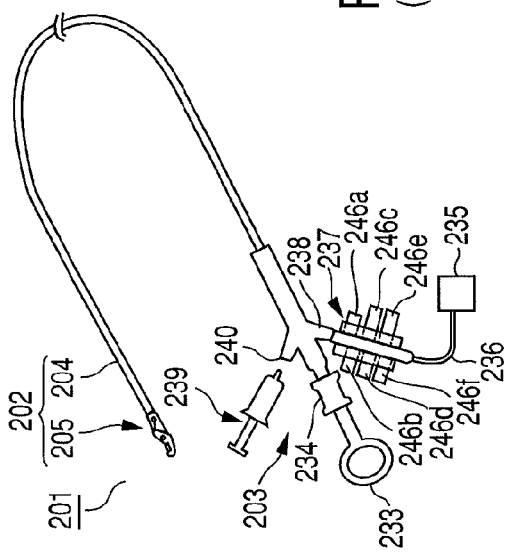
FIG. 17A is a schematic view of a conventional medical instrument.
Figure 17D:
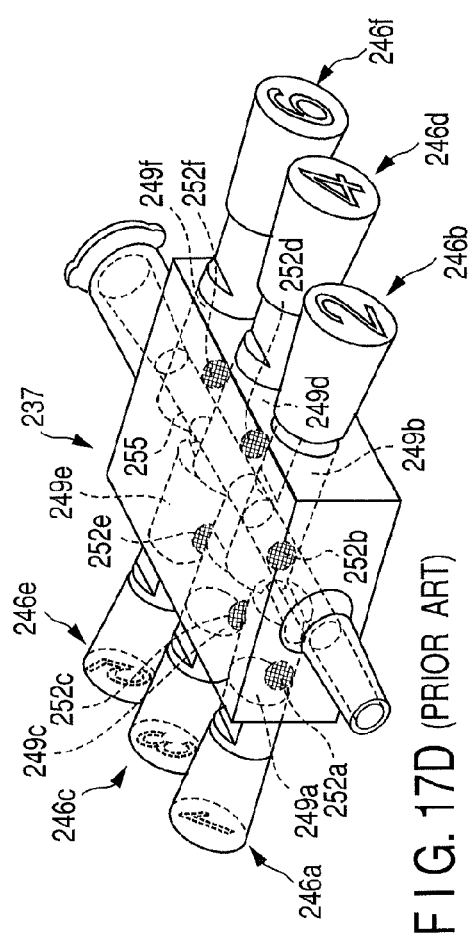
FIG. 17D is a perspective view of a tissue recovery container.

Subsequently, the sheath 4 is pushed into the forceps channel (not shown) of the endoscope with the movable jaws 20a and 20b open, and the respective edge portions 25a and 25b of the movable jaws 20a and 20b are caused to engage the subject tissue 62, as shown in FIG. 12. In this state, the forceps control slider 34 is moved to the proximal end side so that the pair of forceps control wires 9a and 9b are pulled back to the proximal end side. Thereupon, the forceps control wires 9a and 9b are pulled back to the proximal end side, so that the movable jaws 20a and 20b independently rock around the forceps supporting pins 22a and 22b in the direction opposite to the direction of the aforesaid opening operation. Thus, a forceps opening that is defined by the jaws is close. By this operation, the organic tissue 62 is excised, and the excised tissue slice 63a is held in the tissue receiving space 27 of the movable jaws 20a and 20b (see FIG. 13).

When the movable jaws 20a and 20b are fully closed in this manner, the bent portions 64a and 64b of the forceps control wires 9a and 9b are elastically deformed and stretched in a manner such that they touch and interfere with the forceps control wire outlet portions 18a and 18b (see FIG. 13). If the forceps control slider 34 is unhanded so that a force having so far been applied to the forceps control slider 34 (force to pull back the forceps control wires 9a and 9b to the proximal end side) is removed in this state, therefore, the bent portions 64a and 64b of the elastically deformed forceps control wires 9a and 9b are urged to restore their original bent molded shape by the restoring force of the wires. As this is done, the forceps control wires 9a and 9b slightly move to the distal end side to reach a position where the bent portions 64a and 64b never touch or interfere with the forceps control wire outlet portions 18a and 18b. Thereupon, the respective distal ends of the movable jaws 20a and 20b naturally open to an angle wider than about 10° and narrower than 45° (see FIG. 14). In consequence, a part of the tissue slice 63a, excised and recovered, can be released from hold between the edge portions 25a and 25b of the movable jaws 20a and 20b, if any.

Subsequently, the suction control slider 42 is grasped and pulled to the proximal end side. Thereupon, both the push rod 52 and the valve spring 60 are pushed in toward the release tubular line 54 to close the opening on the side of the release tubular line 54, as shown in FIG. 7D, whereupon the sliding tubular line 53 and the release tubular line 54 are disconnected. Accordingly, the negative pressure that acts on the external communication passage 59 is applied to the suction port 38 through the sliding tubular line 53 and the internal communication passage 58. If the suction control slider 42 is released from a tractive effort, the valve spring 60 is restored to its original shape and stretched, whereupon the push rod 52 and the valve seat 57 return to their original positions. Thus, the negative pressure from the return tube 61 is applied to the endoscope through the sliding tubular line 53, release tubular line 54, and return port 56, whereupon the negative pressure on the suction port 38 is removed.

If a fluid for reflux is forced out of the syringe 39 into the liquid conveying port 40 after the syringe 39 filled with the fluid is attached to the liquid conveying port 40, the fluid flows from the liquid conveying port 40 into the residual space 28 in the sheath 4 through the liquid conveying line 41 and reaches the tissue receiving space 27 of the movable jaws 20a and 20b. Since the inner tube 8 and the suction nozzle 13 are negatively pressurized through the suction port 38 on which the negative pressure acts, on the other hand, the tissue slice 63a that is held in the tissue receiving space 27 of the movable jaws 20a and 20b is sucked through the suction nozzle 13 into the inner tube 8 and swept away by the fluid without jamming the inner tube 8. Finally, the tissue slice 63a is sucked through the suction port 38 into the mesh filter 73a of the trap body 70 of the tissue recovery trap 69 and captured. More specifically, the tissue slice 63a, sucked together with the fluid into the inner tube 8, enters the depression 72a and is stopped by the surface of the mesh filter 73a. On the other hand, the fluid passes through the fine orifices of the mesh filter 73a, and is sucked from the suction tube 36 into the negative-pressure generator 35 through the suction line 55, suction port 38, internal communication passage 58, sliding tubular line 53, and external communication passage 59. Further, whether or not the tissue slice 63a is in the depression 72a is visually confirmed through the tissue recognition window 45 of the transparent material behind the rear-side opening seal 44.

If the tissue slice 63a is recognized through the tissue recognition window 45, the finger knob 77 is pressed further to push the trap body 70. As this is done, a bending force acts on the trap body 70. Since its deformation is prevented by the shoulder 83 of the support 71, however, the trap body 70 is restrained from being deformed or broken.

If the trap body 70 is thus pushed in, the plate spring 80 deforms outward, whereupon the protrusions 79a and 79b sink and get out of the recesses 78a. Further, the trap body 70 that holds the tissue slice 63a therein projects from the lower surface of the tissue trap mounting portion 37. It is fixed when the next recesses 78b engage the protrusions 79a and 79b. As this is done, the respective centers of the next depression 72b and the mesh filter 73b are aligned with the respective centers of the inner tube 8, front-side opening seal 43, rear-side opening seal 44, and suction line 55. Thereupon, preparations for the recovery of another tissue slice are completed. In this state, as shown in FIG. 11A, the trap body 70 projects from the lower surface of the tissue trap mounting portion 37 so that its through slits 74a are exposed. If the trap 75a is grasped and bent longitudinally, therefore, the trap 75a can be easily severed from the trap body 70 at the through slits 74a. Thereafter, the trap 75a, holding the tissue slice 63a and severed, is put directly into a sample bottle 59 that contains a tissue fixing agent 61 therein, so that the tissue slice 63a is immersed in the tissue fixing agent 61, as shown in FIG. 11C.

Tissue slices 63b to 63e are also recovered in due order in like manner by the aforesaid operation with use of the other traps 75b to 75e that remain in the trap body 70. After the last trap 75e is severed, the finger knob 77 is held and pulled up, whereupon the trap body 70 and the support 71 are removed entire from the tissue trap mounting portion 37. Even after the traps 75a to 75e are severed, the tissue slices 63a to 63e that are held individually in the traps can be easily discriminated, since the markings 84a to 84e are put on the individual traps.

If more tissue slices are required, another combination of the trap body 70 and the support 71 is prepared and attached to the tissue trap mounting portion 37, and the aforesaid operation is repeated. In this manner, continuous operation for picking the subject tissue of the mucous membrane in the body cavity by means of the medical instrument 1 terminates.

In the medical instrument 1 of the present embodiment, as described above, the forceps control wire holding pins 23a and 23b are situated on or near the reference plane P that passes through the longitudinal central axis O1 and extends parallel to the second rocking axis O2. Accordingly, one end portions (outward end faces) 98 of the forceps control wire holding pins 23a and 23b on the side that face (or is opposed to) the tip cover flat portions 15a and 15b can be formed flat, so that a wide connection space (working space) for the forceps control wires 9a and 9b can be secured. Thus, fixing the forceps control wire holding pins 23a and 23b and the control wires 9a and 9b by laser welding, spreading, etc. has no directivity, so that the workability is improved. Since the pins are arranged in a region that has a maximum outer diameter, moreover, projections from the circumference of a circle can be lessened, so that the maximum outer diameter of the tissue picking portion 5 can be reduced. Thus, the resistance of insertion of the endoscope into the forceps channel lowers, so that the operating efficiency is improved.

Figure 18A:
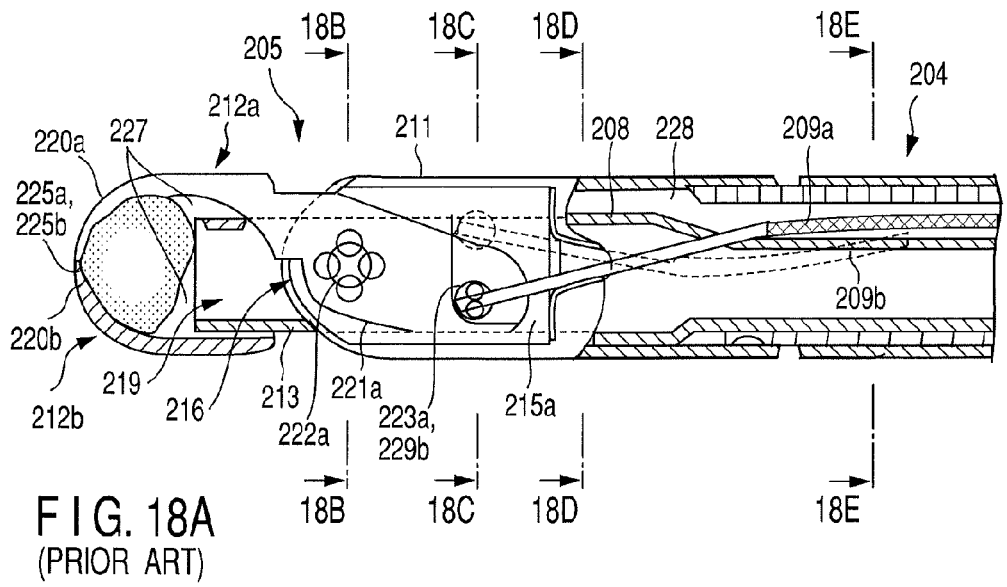
FIG. 18A is a sectional view of the distal end portion of the medical instrument of FIG. 17A.
Figure 18B:
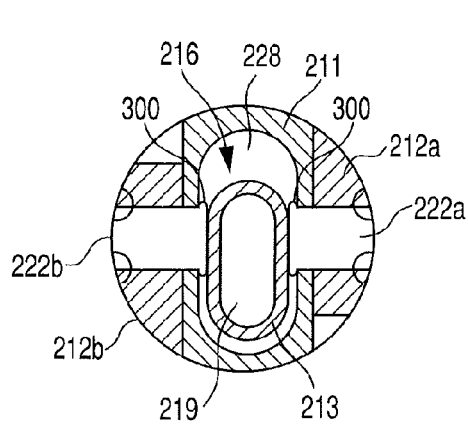
FIG. 18B is a sectional view taken along line 18B-18B of FIG. 18A.
Figure 18C:
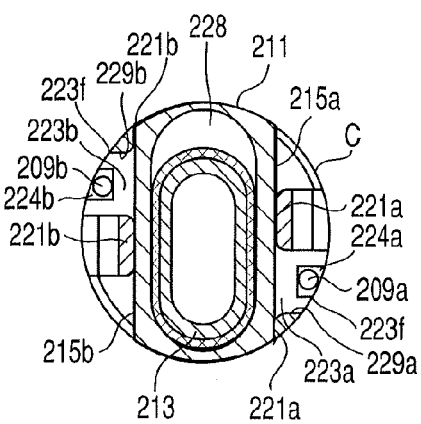
FIG. 18C is a sectional view taken along line 18C-18C of FIG. 18A.
Figure 18D:
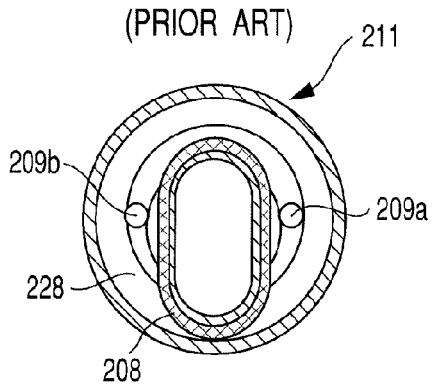
FIG. 18D is a sectional view taken along line 18D-18D of FIG. 18A.
Figure 18E:
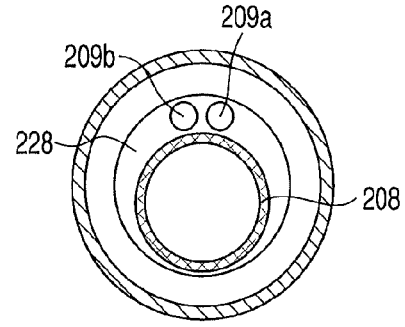
FIG. 18E is a sectional view taken along line 18E-18E of FIG. 18A.
Figure 19:
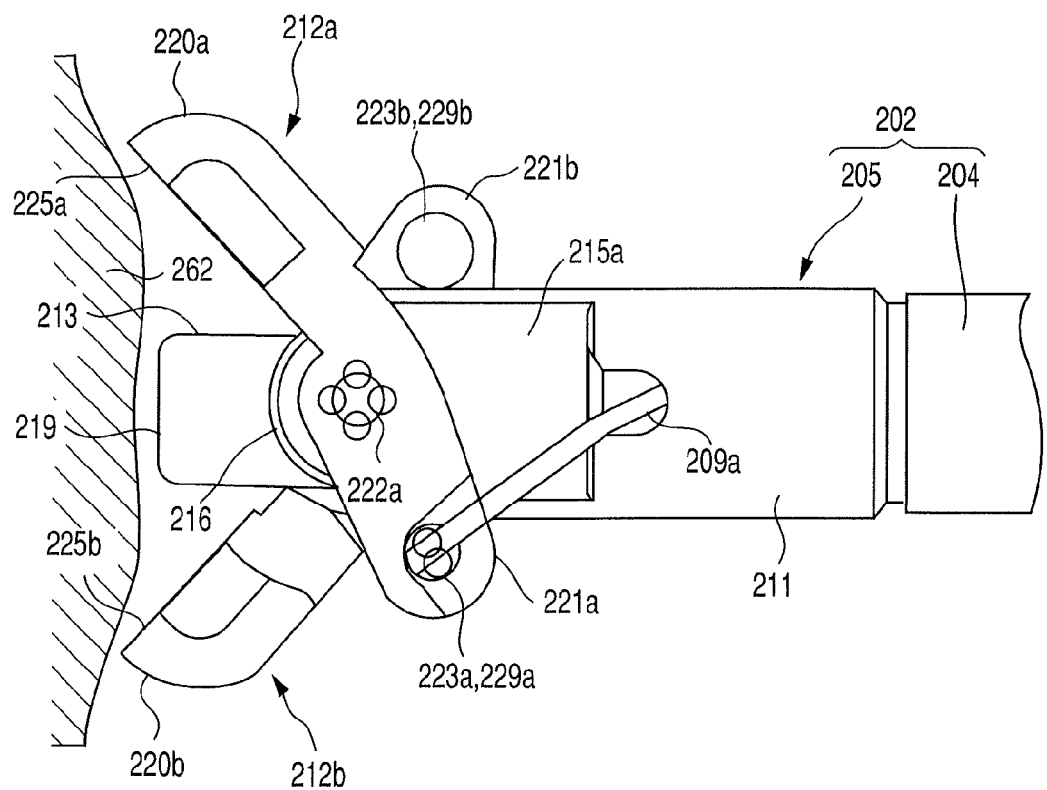
FIG. 19 is a view showing the medical instrument of FIG. 17 having its forceps open and held against a tissue.
Figure 20:
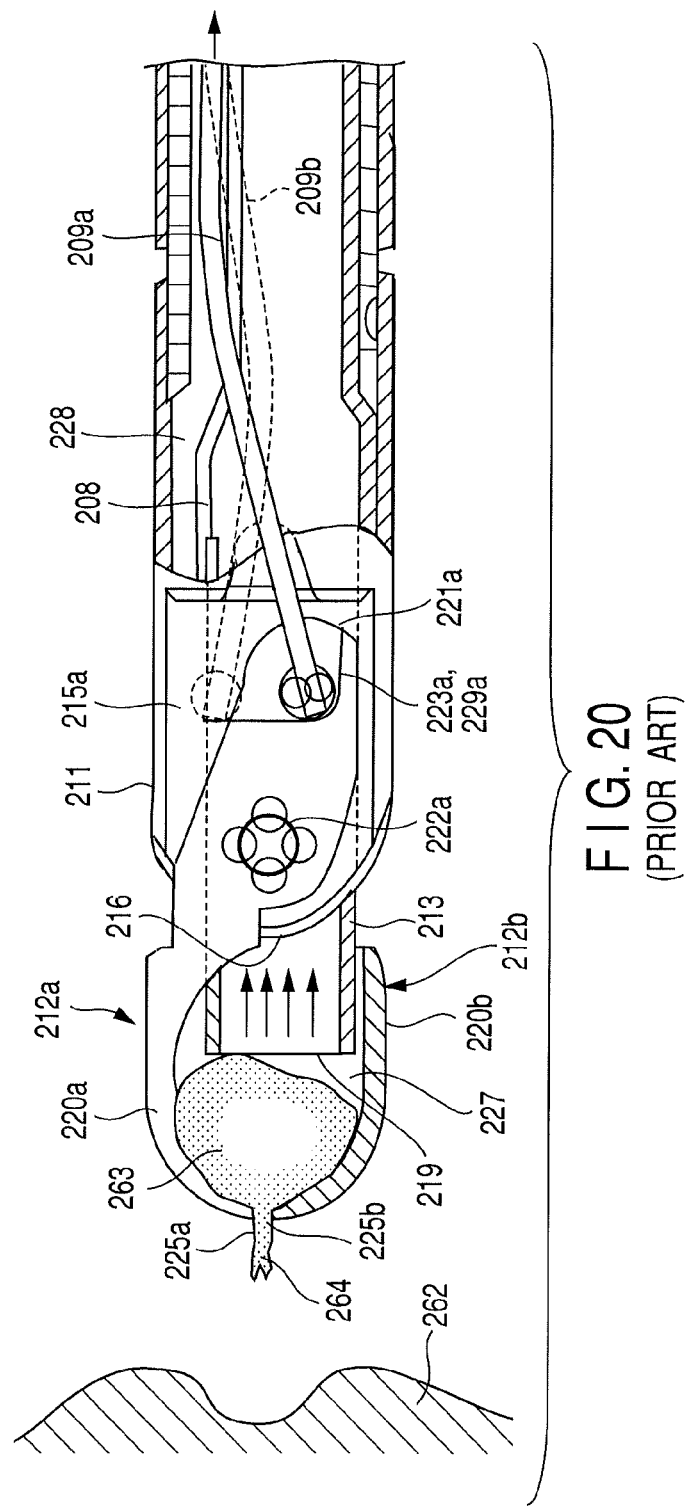
FIG. 20 is a view showing the way the forceps in the state of FIG. 19 are closed to recover and hold a tissue slice therein.

In the configuration described in the aforementioned Jpn. Pat. Appln. KOKAI Publication No. 2000-279418, on the other hand, the forceps control wires 209a and 209b are fixed by spreading, laser welding, etc. after they are passed through the forceps control wire holding grooves 224a and 224b formed in the forceps control wire holding pins 223a and 223b. Since the forceps control wire holding pins 223a and 223b are spaced individually outward from the central axis plane of the forceps (or the plane of contact between the edge portions 225a and 225b of the movable jaws) (that is, the forceps control wire holding pins 223a and 223b are located at a good distance from a plane that passes through the longitudinal central axis of the tissue picking portion 205 (tip cover 211) and extends parallel to the longitudinal central axis of the forceps control wire holding pins 223a and 223b), the outward end faces 223f of the forceps control wire holding pins 223a and 223b are obliquely formed to match the circumferential surface C of the forceps (see FIG. 18C). This is done because the outer diameter of the medical instrument must be made smaller than the inner diameter of the forceps channel of the endoscope, since the instrument is inserted in the forceps channel when it is used. In fixing the forceps control wires 209a and 209b to the forceps control wire holding grooves 224a and 224b in the forceps control wire holding pins 223a and 223b by spreading or laser welding, however, a satisfactory connection space (working space) for the forceps control wires 209a and 209b cannot be secured with use of an inclined working plane. Thus, positioning and fixing operations are harder than when a substantially horizontal plane is used. Naturally, in order to give priority to workability, the respective outward end faces 223f of the forceps control wire holding pins 223a and 223b may possibly be formed to be substantially horizontal surfaces in the state of FIG. 18C where the forceps control wire holding pins 223a and 223b are spaced outward from the central axis plane of the forceps. In this case, however, the corner portions of the substantially horizontal surfaces project from the circumferential surface, so that the maximum outer diameter increases. Thus, the resistance of insertion into the endoscope is so high that the operating efficiency lowers.

In the medical instrument 1 of the present embodiment, moreover, the forceps supporting pins 22a and 22b that have the first rocking axis O1 are formed integrally with the flat portions 15a and 15b. As is also evident from FIG. 4B, therefore, the forceps supporting pins 22a and 22b never project into the bore of the tip cover 11. Thus, the size of the suction nozzle 13 that is passed through the bore of the tip cover 11 cannot be restricted.

Further, the medical instrument 1 of the present embodiment is formed having a plurality of bent portions 64a and 64b as springy molded parts near the respective distal ends of the forceps control wires 9a and 9b, that is, in sections from the forceps control wire holding pins 23a and 23b to the forceps control wire outlet portions 18a and 18b. The bent portions 64a and 64b are formed having a shape such that they never interfere with the forceps control wire outlet portions 18a and 18b when the respective distal ends of the movable jaws 20a and 20b are inclined at an angle less than 45° and not less than 10°. If the movable jaws 20a and 20b are fully closed, on the other hand, the bent portions 64a and 64b are brought into contact with the forceps control wire outlet portions 18a and 18b, whereby the bent portions 64a and 64b are elastically deformed. Thus, if the operator releases his/her hold of the forceps control slider 34 so that no operating force acts on it, the respective distal ends of the movable jaws 20a and 20b automatically open at an angle less than 45° and not less than 10°. If a negative pressure is applied to the suction nozzle 13 in this state, the tissue slice 63a is pulled into the suction nozzle 13 without being nipped between the edge portions 25a and 25b. Thus, the tissue slices 63a, . . . can be securely sucked in and recovered without any special operation by the operator.

In the medical instrument 1 of the present embodiment, moreover, the suction port 19 at the distal end of the suction nozzle 13 has an outer diameter such that it can be held in the tissue receiving space 27 of the movable jaws 20a and 20b. Further, the proximal end side portion 85 of the suction nozzle 13 has an oval cross section of an area wide enough to allow the passage of the tissue slice 63a. Furthermore, the taper portion 86 is formed on the transit section from the suction port 19 to the proximal end side portion 85. The taper portion 86 has a smooth surface that connects the suction port 19 having a circular cross section and the inner surface of the proximal end side portion 85. Thus, the tissue slices 63a, . . . that are held in the tissue receiving space 27 of the jaws 20a and 20b can smoothly deform and pass through the suction port 19, taper portion 86, and proximal end side portion 85 without jamming. If the tissue slices 63a, . . . have sizes that match the capacity of the tissue receiving space 27, therefore, they can be securely recovered without damage.

In the configuration described in the aforementioned Jpn. Pat. Appln. KOKAI Publication No. 2000-279418, on the other hand, the suction port 219 at the distal end of the suction nozzle 213 has an oval shape that matches the opening portion 216 of the tip cover 211, which is smaller than the cross section of the tissue receiving space 227 of the movable jaws 220a and 220b. If the tissue receiving space 227 of the movable jaws 220a and 220b is filled with the picked tissue slice 263, therefore, pulling the tissue slice 263 into the suction port 219 requires deformation under suction pressure. Thus, the edge of the suction port 219 may possibly damage the tissue slice 263. If the tissue slice is hard, it cannot be deformed and may possibly remain in the tissue receiving space 227 of the movable jaws 220a and 220b without being recovered.

In the present embodiment arranged in this manner, however, the tissue slices 63a, . . . that are excised by means of the forceps are gradually deformed as they are attracted to the suction port 19 by suction and pass through the taper portion 86. Finally, the tissue slice is deformed to a diameter such that it can get into the inner tube 8, and is sucked into the inner tube 8.

Further, the control section body 31 of the medical instrument 1 of the present embodiment is provided with the tissue trap mounting portion 37. The mounting portion 37 can receive the trap body 70, which has the mesh filters (filter elements) 73a to 73e and chambers that hold the tissues. The trap body 70 can be divided into the individual traps 75a to 75e. Thus, the tissue slices 63a to 63e can be held individually, and the mesh filters 73a to 73e can be changed on the course of the inner tube 8 by simple operation. Further, the tissue slices 63a to 63e can be handled with ease, so that the operator's labor can be saved, and the working time can be shortened.

In the configuration described in the aforementioned Jpn. Pat. Appln. KOKAI Publication No. 2000-279418, on the other hand, a plurality of vials 246a to 246f are attached to the housing of the tissue recovery container 237. In recovering a plurality of tissues, however, mesh filters 252a to 252f must be caused to project over the suction line 255 by suitably pushing in the vials 246a to 246f in the order based on the vicinity to the distal end. Since these vials are located close to one another, they may possibly be pushed wrongly or in a wrong order. If the vials 246a to 246f are pushed in a wrong order, it is hard to match the regions of patient's body from which a plurality of tissue slices are picked to records. Thus, accurate diagnosis may possibly be hindered.

In the medical instrument 1 of the present embodiment, moreover, the tissue recognition window 45 is formed of a transparent material, so that whether or not the tissue slices 63a, . . . are captured by the mesh filters 73a to 73e can be visually confirmed. Thus, whether or not the tissue slices 63a, . . . are recovered can be confirmed without moving the trap body 70, so that the working time can be shortened by the omission of a step of operation. In the present embodiment, the tissue receiving space 27 of the movable jaws 20a and 20b, the mesh filters 73a to 73e, and a part of the trap body 70 may be formed of a transparent material. In this case, whether or not the tissue slices 63a, . . . are captured can be visually confirmed from the outside, so that whether or not the tissue slices 63a, . . . are recovered can be confirmed without moving the trap portion. Thus, the working time can be shortened by the omission of a step of operation.

In the medical instrument 1 of the present embodiment, furthermore, the suction control slider 42 is supported by means of the supporting rod 32 of the instrument control section and is slidable just behind the forceps control slider 34. Further, the valve spring 60 and the push rod 52 engage the suction control slider 42, and application of the negative pressure from the return port 56 to the suction port 38 can be switched by axially moving the valve seat 57 that is fixed to the push rod 52. Accordingly, unloading the force to pull the forceps control slider 34 and switching the negative pressure application can be achieved simultaneously and alternatively by simply releasing the hold of the forceps control slider (first movable slide member) 34 and pulling the suction control slider (second movable slide member) 42 toward the proximal end side. Thus, the movable jaws 20a and 20b can be automatically opened to ensure smooth suctional recovery operation only while the negative pressure is acting on the suction port 38.

With the conventional medical instrument, the operator manipulates the forceps control slider 34 only. In general, therefore, the forceps control slider 34 is often kept held while a tissue slice is being held. Therefore, release of the forceps control slider 234 requires some experience and may possibly result in wrong operation as the tissue slice 263 leaves the nipped tissue and is drawn in to a position within reach by suction. According to the present embodiment, however, this problem can be solved.

In the present embodiment, moreover, the liquid conveying port 40 is located near the suction control slider 42 and in the vicinity of the proximal end of the supporting rod 32. While the fluid is being delivered with the syringe 39 mounted in position, therefore, the operator holds the grip ring 33 and the suction control slider 42 with a pull. Therefore, the region in which the operator holds the instrument control section 3 is situated close to the point of operation on the fluid delivery portion, so that the syringe 39 can be easily pushed in with a greater force.

In the configuration described in the aforementioned Jpn. Pat. Appln. KOKAI Publication No. 2000-279418, on the other hand, the liquid conveying port 240 to which the syringe 239 for delivering the fluid into the residual space 228 in the sheath 204 is attached is set in a position nearer to the distal end of the control section body 231. When the fluid is actually delivered, however, the position for the operation to push in the piston of the syringe 239 is distant from the position (of the grip ring 233 and the forceps control slider 234) in which the medical instrument is held, so that the manipulation is not easy. If there is a distance between these two points, moreover, a bending force acts on the control section 3, and furthermore, the holding operation may possibly be laborious.

In the present embodiment, moreover, the ring valve body 47 has therein the inner tube 8 of the biopsy forceps and a valve function that alternatively connects the suction connector (not shown) of the endoscope to the negative-pressure generator 35. For the valve function, there are provided the push rod 52, valve seat 57, sliding tubular line 53, release tubular line 54, internal communication passage 58, external communication passage 59, and valve spring 60. When the suction control slider 42 is not operating, therefore, the push rod 52 and the valve seat 57 are urged in one direction by the restoring force of the valve spring 60. Thereupon, a negative pressure from the negative-pressure generator 35 is applied to the endoscope through the return tube 61 via the sliding tubular line 53, release tubular line 54, and return port 56. Thus, suction of the endoscope can be used normally. If the suction control slider 42 is pulled toward the proximal end side, on the other hand, the push rod 52 and the valve seat 57 are actuated, whereupon the negative pressure is applied to the interior of the inner tube 8 through the sliding tubular line 53 and the internal communication passage 58. Thus, the destination of the negative pressure from the negative-pressure generator 35 can be switched to the endoscope or the biopsy forceps by simple operation to switch the suction control slider 42 on or off. In consequence, the steps of procedure of the operation can be simplified, and an effect can be expected that there is no possibility of wrong operation.

In the configuration described in the aforementioned Jpn. Pat. Appln. KOKAI Publication No. 2000-279418, on the other hand, the tissue recovery container 237, suction tube 236, and suction means 235 are connected directly to one another. Thus, a dedicated device for the medical instrument is indispensable as the suction means 235. General hospital facilities are provided with suction means to be connected to an endoscope for treatment. However, few of them can prepare dedicated suction means for the medical instrument. In using the medical instrument 1 with suction means for endoscope, therefore, many hospital facilities solve this problem by using a valve unit for suitably switching the endoscope over to the medical instrument. The medical instrument 1 requires the use of the suction means 35 for only a moment before the tissue slice 263 is recovered. Preferably, therefore, the suction means 235 should be kept connected to the endoscope at any other time. The present embodiment can solve or remove these problems and troubles.

FIGS. 15A to 16D show a second embodiment of the present invention. The present embodiment is a modification of the first embodiment. In the description to follow, therefore, like numerals are used to designate components that are shared by the first embodiment, and a description of those components is omitted.

In the present embodiment, support holes 112a and 112b of forceps 12a and 12b have a diameter larger than that of forceps supporting pins 22a and 22b that are formed integrally with flat portions 15a and 15b of a tip cover 11. On the other hand, stopper pins 115a and 115b have an inner diameter such that they can receive the forceps supporting pins 22a and 22b and an outer diameter such that they can be inserted into the support holes 112a and 112b. Their respective first ends are formed having collar portions (spread portions) 113a and 113b. Thus, in the present embodiment, the tubular pins 115a and 115b are arranged so that they are fitted on the forceps supporting pins 22a and 22b that define a first rocking axis O1. The pins 115a and 115b are composed of shank portions 114a and 114b and the spread portions 113a and 113b, respectively (see FIG. 15A). The shank portions 114a and 114b have inner and outer diameters such that they can be fitted between the respective inner surfaces of the support holes 112a and 112b of the forceps 12a and 12b and the forceps supporting pins 22a and 22b to support the forceps 12a and 12b, respectively. The spread portions 113a and 113b are formed on the respective distal ends of the shank portions 114a and 114b that project from the support holes 112a and 112b, respectively. Their outer diameter is larger than that of the shank portions 114a and 114b.

After the forceps supporting pins 22a and 22b are passed through the support holes 112a and 112b of the forceps 12a and 12b, respectively, in this configuration, the stopper pins 115a and 115b are inserted. The boundaries between the forceps supporting pins 22a and 22b and the collar portions 113a and 113b are welded and unified by laser welding or the like. Thereupon, the forceps 12a and 12b are supported on the flat portions 15a and 15b of the tip cover 11, respectively, for rocking motion.

Besides the effect of the first embodiment, according to this configuration, the collar portions 113a and 113b can be formed by welding without mechanically spreading the forceps supporting pins 22a and 22b, so that the productivity can be improved, and the possibility of material deformation that is attributable to mechanical spreading can be eliminated.

In the configuration described in the aforementioned Jpn. Pat. Appln. KOKAI Publication No. 2000-279418, on the other hand, the forceps supporting pins 222a and 222b are held penetrating the flat portions 215a and 215b of the tip cover 211. After the forceps 212a and 212b are supported from outside, the respective distal ends of the forceps supporting pins 222a and 222b are spread and fixed by laser welding or the like, whereby the forceps 212a and 212b and the forceps supporting pins 222a and 222b are fixed integrally to one another. However, the respective head portions of the forceps supporting pins 222a and 222b project into the bore of the tip cover 211. Owing to the presence of these head portions, the width of the suction nozzle 213 with an oval cross section, which is also set in the bore of the tip cover, must be lessened. This is unfavorable because the deformation increases as a tissue slice is sucked into the bore of the suction nozzle 213. As the forceps 212a and 212b rotate, moreover, the outer peripheral surface of the suction nozzle 213 may touch the head portions of the forceps supporting pins 222a and 222b. Owing to frictional resistance produced in these parts, therefore, the operation may possibly slow down.

It is to be understood that the present invention is not limited to the embodiments described above, and that various changes and modifications may be effected therein without departing from the scope or spirit of the invention. In the embodiments described above, for example, the control wires 9a and 9b are connected directly to the forceps 12a and 12b by means of the pins 23a and 23b. Alternatively, however, the control wires 9a and 9b may be connected to the forceps 12a and 12b by means of a link mechanism or the like.

What is claimed is:

1. A medical instrument comprising:
   a swingable operating section formed of a pair of forceps, each of which rocks individually around a first axis corresponding thereto;
   a tubular sheath having a distal end portion situated on a proximal end side of the operating section, the distal end portion having a circular-section portion having a circular cross section perpendicular to a longitudinal central axis of the tubular sheath and a pair of parallel flat portions symmetrically formed on opposite sides of the circular-section portion and in sliding contact with respective proximal end portions of the forceps;
   a pair of manipulators which advance and retreat along the longitudinal central axis of the tubular sheath, thereby rocking the forceps around the first axis; and
   a pair of junctions which respectively connect each of the pair of manipulators to a corresponding end portion of one of the pair of forceps, wherein each of the junctions is rotatable around a second axis,
   wherein each of the junctions is situated on a reference plane containing the longitudinal central axis of the tubular sheath and extending parallel to the second rocking axes, when the operating section is closed.

2. A medical instrument according to claim 1, wherein the junctions are situated in a region that has a maximum outer diameter of the circular-section portion when the operating section is closed.

3. The medical instrument according to claim 1, wherein the first axis of each forceps is not on the reference plane when the operating section is closed.

4. The medical instrument according to claim 1, wherein the second axes are apart from the reference plane when the operating section is opened.

5. The medical instrument according to claim 1, wherein the manipulators are made of stainless spring steel or a superelastic wire material.

6. The medical instrument according to claim 1, wherein the tubular sheath has a port formed at a distal end of the distal end portion to outwardly open, and a bore extending along the longitudinal central axis and communicated with the port.

7. The medical instrument according to claim 1, wherein the manipulators include a pair of wires and the junctions include a pair of pins, which are respectively connected to the wires.

* * * * *